United States Patent
Takino et al.

(10) Patent No.: US 8,500,710 B2
(45) Date of Patent: Aug. 6, 2013

(54) ABSORBENT ARTICLE

(75) Inventors: Shunsuke Takino, Kagawa (JP); Yuki Maeda, Kagawa (JP); Hiroyuki Tanji, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 532 days.

(21) Appl. No.: 12/676,437

(22) PCT Filed: Aug. 13, 2008

(86) PCT No.: PCT/JP2008/064534
§ 371 (c)(1),
(2), (4) Date: Jun. 11, 2010

(87) PCT Pub. No.: WO2009/031393
PCT Pub. Date: Mar. 12, 2009

(65) Prior Publication Data
US 2010/0286646 A1 Nov. 11, 2010

(30) Foreign Application Priority Data

Sep. 5, 2007 (JP) ................. 2007-230640
Sep. 5, 2007 (JP) ................. 2007-230709
Sep. 6, 2007 (JP) ................. 2007-232015

(51) Int. Cl.
*A61F 13/15* (2006.01)
(52) U.S. Cl.
USPC .......... 604/385.24; 604/385.25; 604/385.26; 604/385.27; 604/385.29; 604/385.3
(58) Field of Classification Search
USPC ............ 604/385.24, 385.25, 385.26, 385.27, 604/385.29, 385.3
See application file for complete search history.

(56) References Cited

U.S. PATENT DOCUMENTS

| 4,515,595 | A | 5/1985 | Kievit et al. |
| 7,060,058 | B2 | 6/2006 | Otsubo et al. |
| 2004/0015146 | A1* | 1/2004 | Torigoshi et al. ........ 604/385.27 |
| 2005/0131366 | A1 | 6/2005 | Shimada |

FOREIGN PATENT DOCUMENTS

| GB | 2 253 131 A | 9/1992 |
| JP | 59-54509 U | 4/1984 |
| JP | 59-144601 | 8/1984 |
| JP | 2000-189462 A | 7/2000 |
| JP | 2002-306534 A | 10/2002 |

(Continued)

OTHER PUBLICATIONS

PCT/JP2008/064534 International Search Report mailed Nov. 25, 2008.

*Primary Examiner* — Jacqueline F. Stephens
(74) *Attorney, Agent, or Firm* — Lowe Hauptman Ham & Berner, LLP

(57) ABSTRACT

An absorbent article includes a belt member defining front and rear waist regions and a liquid-absorbent structure defining a crotch region wherein the belt member includes a peripheral edge of a waist-opening and this peripheral edge includes two segments associated with the front and rear waist regions spaced from and opposed to each other in an anteroposterior direction Y. Front and rear belt sections of the belt member include, in the front and rear waist regions, see-through regions for the article wearer's skin having a total light transmittance of about 55% or higher and occupying 40% or more of the front and rear waist regions. The front and rear belt sections are provided along the peripheral edge of the waist-opening with a reinforcing elastic member extending in a transverse direction X.

13 Claims, 21 Drawing Sheets

FOREIGN PATENT DOCUMENTS

| | | |
|---|---|---|
| JP | 2004-141640 A | 5/2004 |
| JP | 2004-329238 A | 11/2004 |
| JP | 2005-218674 A | 8/2005 |
| WO | 2006/017718 A1 | 2/2006 |

* cited by examiner

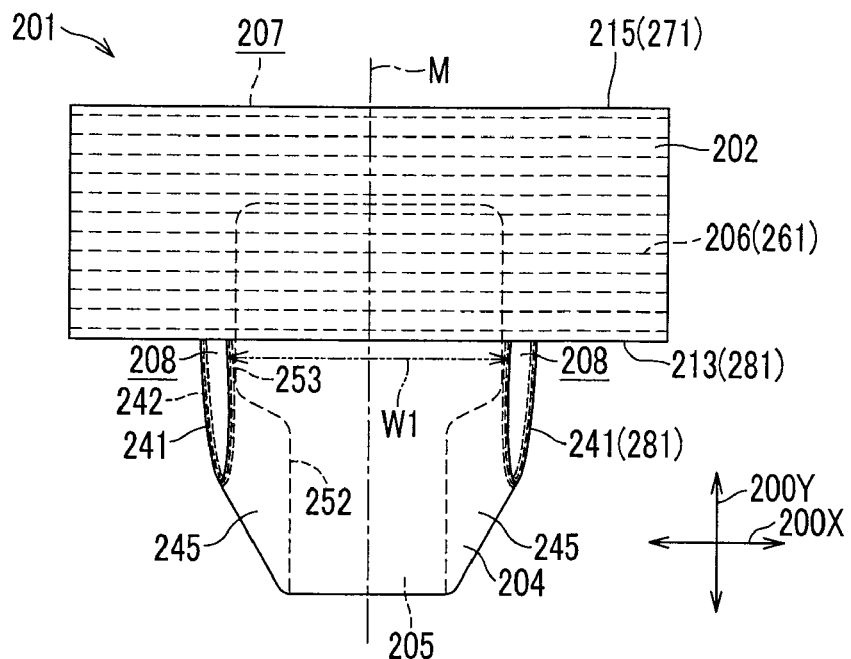
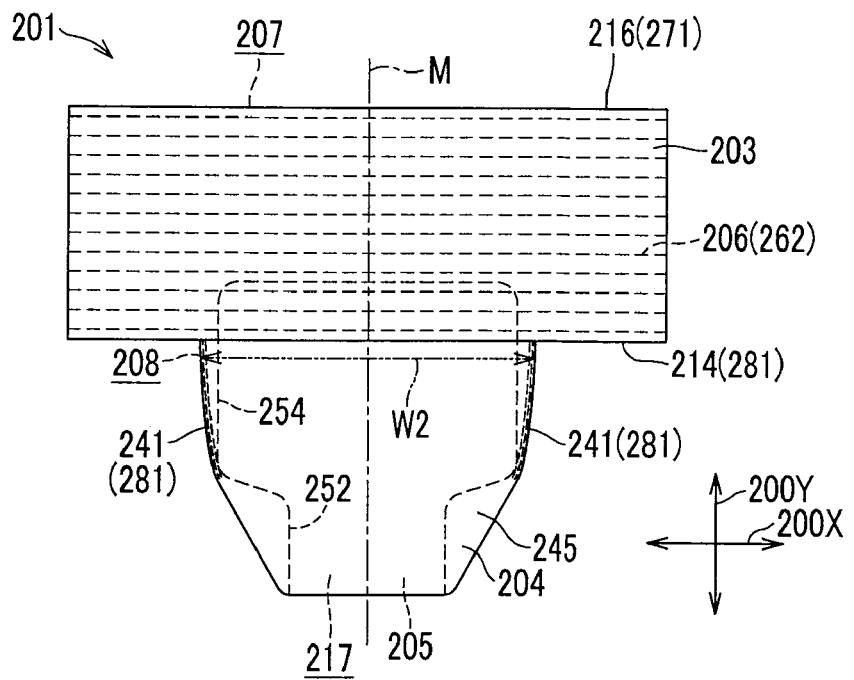

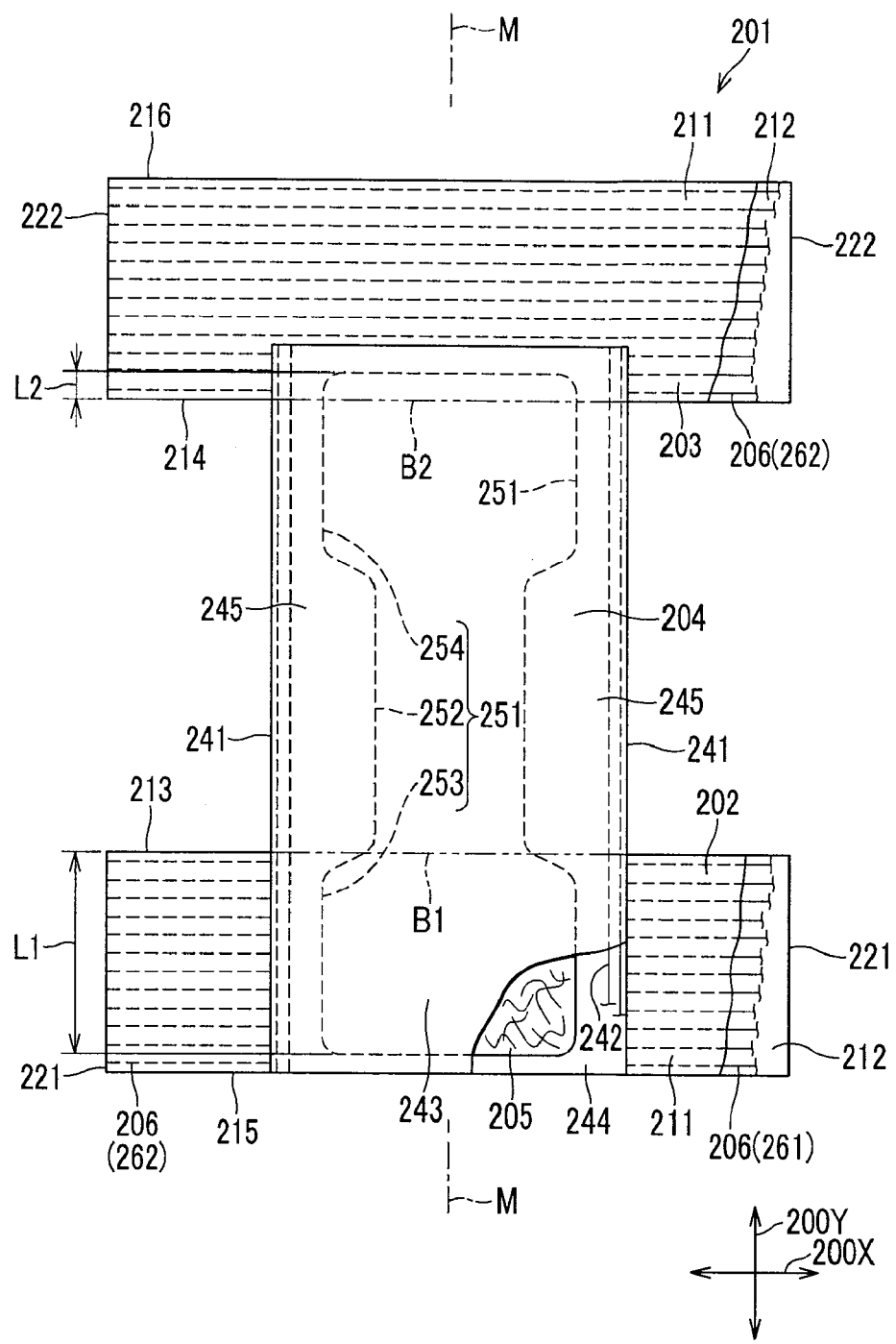

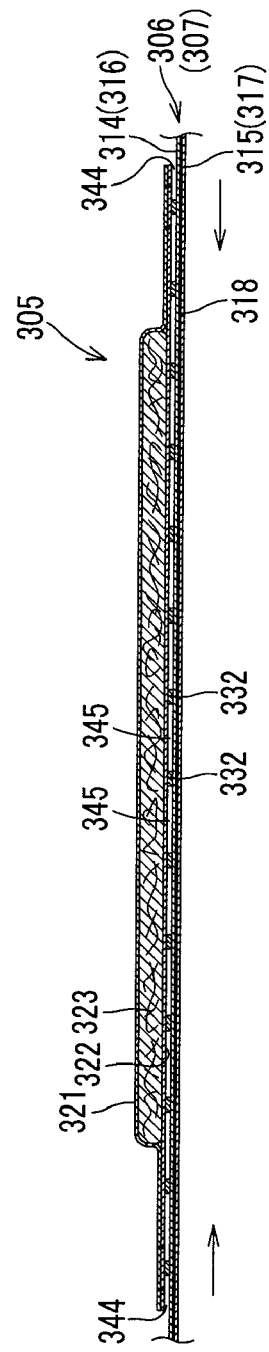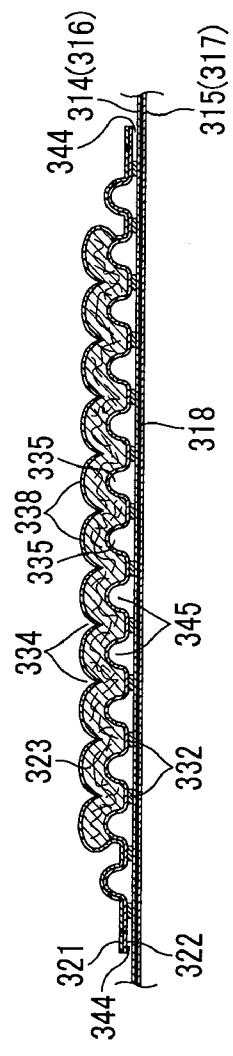

FIG. 25
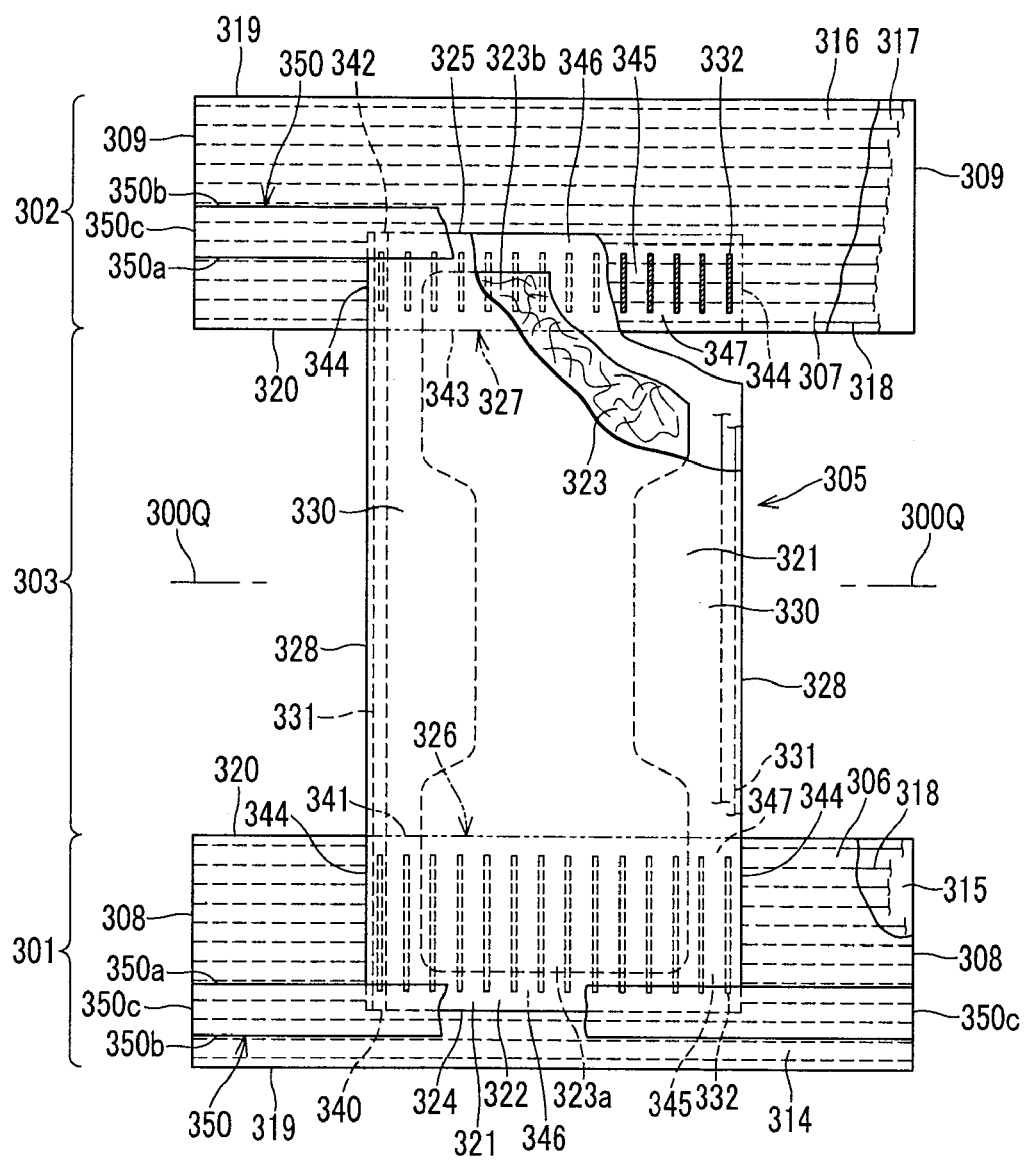
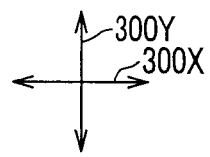

ABSORBENT ARTICLE

RELATED APPLICATIONS

The present application is based on International Application PCT/JP2008/064534, filed Aug. 13, 2008 and claims priority from Japanese Application No. 2007-230640, filed Sep. 5, 2007, Japanese Application No. 2007-230709, filed Sep. 5, 2007 and Japanese Application No. 2007-232015, filed Sep. 6, 2007, the disclosures of which are hereby incorporated by reference herein in their entirety.

TECHNICAL FIELD

The present invention relates to absorbent article such as disposable diapers, toilet-training pants and incontinent briefs.

RELATED ART

Disposable diapers intended to make their inside see-through are well known, for example, from Japanese Unexamined Patent Application Publication No. 2004-141640 (PATENT DOCUMENT 1). The diaper disclosed in PATENT DOCUMENT 1 is configured from a front waist region, a rear waist region and a crotch region and comprises a liquid-absorbent chassis having an inner side facing the wearer's skin and an outer side facing the wearer's garments, and waist elastic members attached to the front and rear waist region so as to extend in a transverse direction. The liquid-absorbent chassis comprises, in turn, an inner sheet facing the wearer's skin and an outer sheet facing the wearer's garments wherein at least the outer sheet is formed by a fibrous nonwoven fabric with fiber fineness as well as basis weight thereof sufficiently reduced to enhance light transmittance. By enhancing the light transmittance in this manner, the inside of the diaper can be made see-through.
PATENT DOCUMENT 1: Japanese Unexamined Patent Application Publication No. 2004-141640

As one of various types of disposable diapers, a diaper comprising three substantially rectangular sheets joined together in an I- or H-shape (referred to hereinafter as three-piece type diaper) is well known.

The three-piece type diaper advantageously reduces the cost of production particularly because substantially none of waste pieces is generated during a process of making the diaper of this type. However, it has been difficult for the diaper of this type to cover the wearer's crotch region and buttocks in an appropriate manner since the rectangular sheet is allotted to cover the wearer's crotch region. More specifically, the sheet having a width dimensioned to cover the wearer's crotch region in the appropriate manner is too small to cover the wearer's buttocks and the sheet having a width dimensioned to cover the wearer's buttocks completely become uncomfortably bulky in the wearer's crotch region.

Taking account of such problem, WO 2006/017718 A1 (Claim 1; FIGS. 1 and 7) (PATENT DOCUMENT 2) discloses a pants-type diaper comprising a front waist panel and a rear waist panel opposed to and spaced from each other and a crotch panel provided between these front and rear waist panels wherein these front and rear waist panels are joined to each other along opposite side edges of the front waist panel and opposite side edges of the rear waist panel are jointed so as to form a waist-opening and a pair of leg-openings characterized in that a belt width of the rear waist panel is dimensioned to be larger than a belt width of the front waist panel. As will be seen in FIG. 1 of PATENT DOCUMENT 1, the waist-opening is defined by respective uppermost edges (distal edges) of the front waist panel and the rear waist panel and the paired leg-openings are defined by respective lowermost edges (proximal edges) of the front waist panel and the rear waist panel cooperating with opposite side edges of the crotch panel, respectively.
PATENT DOCUMENT 2: WO 2006/017718 A1 (Claim 1; FIGS. 1 and 7)

Disposable diapers designed to allow the amount of vapor generated in the diaper to be reliably guided to the exterior is well known, for example, from the disclosure of Japanese Unexamined Patent Application Publication No. 1984-144601 (PATENT DOCUMENT 3).

The diaper disclosed in PATENT DOCUMENT 3 comprises a topsheet facing the wearer's skin, a backsheet facing the wearer's garment and the elastic film sandwiched between these top- and backsheets so that the waist-opening may be biased to shrink in a waist line direction by the elastic film. The elastic film is joined to the top- and backsheets intermittently as viewed in a transverse direction. The regions of the top- and backsheets in which the elastic film is not joined to these two sheets sag under contraction of the elastic film to form open channels between these two sheets. Vapor generated in the diaper is guided out through these open channels from the diaper to the exterior.
PATENT DOCUMENT 3: Japanese Unexamined Patent Application Publication No. 1984-144601

DISCLOSURE OF THE INVENTION

Problem to be Solved by the Invention

With respect to PATENT DOCUMENT 1, it is usually desired for the absorbent article such as disposable diapers not only to be highly air-permeable but also to be cool to the eye, particularly in a hot weather area as well as in hot weather season. To satisfy such desires, it has been contemplated to reduce the fibrous fineness and the basis weight of the fibrous nonwoven fabric constituting the chassis in the front and rear waist regions to enhance the light transmittance thereof so that the wearer's skin may be seen through the chassis. However, the fibrous nonwoven fabric having fibrous fineness and basis weight thereof reduced for such purpose may often reduce tensile strength as well as tear strength thereof with a result that the diaper may tear easily. Particularly along a peripheral edge of the waist-opening necessarily exposed to repeated stretching and contraction, such possibility of readily tearing may be significant.

In view of the problem as has been described above, it is an object of the present invention on a first aspect thereof to provide an absorbent article improved so that the article has a well tear resistance and allows the wearer's skin to be seen through the absorbent article.

Certainly the diaper disclosed in PATENT DOCUMENT 2 is capable of covering the wearer's buttocks over a sufficient extent since the belt width thereof is dimensioned to be larger. However, such differential dimension inevitably results in that the rear waist panel has its parts not joined to the front waist panel. With the diaper put on the wearer's body, the parts of the rear waist panel remaining not joined to the front waist panel may often left out of contact with the wearer's buttocks and may not ensure a desired fit of the parts to a region defined between the buttocks to the legs. Furthermore, the diaper shaped in I- or H-shape from three rectangular sheets necessarily forms a pair of the leg-openings on both sides of the wearer's body so as to be parallel to each other. It should be noted here that a movable range of the human legs principally extends forward relative to the torso of the wearer and therefore the leg-openings should preferably open slightly forward.

In view of the problem as has been described above, it is an object of the present invention on a second aspect to provide a diaper of three-piece type improved to ensure a desired fit of the diaper to the wearer's torso particularly in the region defined between the buttocks to the legs.

In the case of the diaper disclosed in PATENT DOCUMENT 3, each of the open channels has one end exposed to the exterior and the other end terminated in the vicinity of the liquid-absorbent structure. In other words, the other end of the open channel does not extend to the liquid-absorbent structure. Consequentially, it has been difficult for these open channels to guide the amount of vapor generated from the liquid-absorbent structure in the crotch region to the exterior while it is possible for these open channels to guide the amount of vapor staying in the vicinity of the waist-opening, more exactly, the amount of vapor staying between the liquid-absorbent structure and the waist-opening, to the exterior.

In view of the problem as has been described above, it is an object of the present invention on a third aspect thereof to provide an absorbent article allowing the amount of vapor generated in the article to be sufficiently guided out from the article to the exterior to alleviate a feeling of wetness otherwise experienced by the wearer.

Measure to Solve the Problem

On the first aspect of the present invention, the object set forth above is achieved by an improvement in the absorbent article comprising a chassis having a longitudinal direction and a transverse direction, an inner side facing the wearer's skin and an outer side facing the wearer's garment, a front waist region, a rear waist region and a crotch region extending between the front and rear waist regions.

The improvement according to the first aspect of the present invention is characterized in that the chassis includes a peripheral edge of a waist-opening consisting of two segments associated with the front and rear waist regions and spaced from and opposed to each other in the longitudinal direction and see-through regions in the front and rear waist regions in which the wearer's skin can be seen through the article, the see-through regions are defined by sheets having a total light transmittance of about 55% or higher and respectively occupy about 40% or more of the front and rear waist regions, and reinforcing means against tear of the chassis is attached to the article along the peripheral edge of the waist-opening so as to extend in the transverse direction.

According to one preferred embodiment of the invention on the first aspect thereof, the chassis includes inner sheets defining respective inner sides of the front and rear waist regions facing the wearer's skin and outer sheets defining outer sides of the front and rear waist regions facing the wearer's garment, and the reinforcing means comprises an elastic member adapted to bias the front and rear waist regions to contract in the transverse direction and attached under tension between the inner sheet and the outer sheet.

According to another preferred embodiment of the invention on the first aspect thereof, the inner and outer sheets are formed from a single fibrous nonwoven fabric folded back onto itself and the peripheral edge of the waist-opening is defined by a fold line along which the fibrous nonwoven fabric is folded back onto itself.

According to still another preferred embodiment of the invention on the first aspect thereof, the front and rear waist regions are provided with a plurality of waist elastic members arranged intermittently as viewed in the longitudinal direction and extending in the transverse direction.

According to yet another preferred embodiment of the invention on the first aspect thereof, the chassis includes a liquid-absorbent structure provided at least in the crotch region, the liquid-absorbent structure includes a first end portion and a second end portion opposed to and spaced from each other in the longitudinal direction, the first end portion is joined to the front waist region by means of a first joint region and the second end portion is joined to the rear waist region by means of a second joint region, and the see-through regions are defined by sub-regions of the front and rear waist regions in which the liquid-absorbent structure is absent.

On the second aspect of the present invention, the object set forth above is achieved by an improvement in the absorbent article substantially symmetric about a longitudinal center line thereof and comprising a longitudinal direction and a transverse direction orthogonal to the longitudinal direction, a ventral sheet member and a dorsal sheet member extending in parallel to each other in the transverse direction, and a crotch sheet member extending in the longitudinal direction and joined to the ventral sheet member and the dorsal sheet member so as to connect these ventral and dorsal sheet members to each other wherein the crotch sheet member has a transverse dimension smaller than those of the ventral and dorsal sheet members.

The improvement according to the second aspect of the present invention is characterized in that the ventral sheet member and the dorsal sheet member are provided with waist elastic members bonded thereto under tension in the transverse direction, at least a region of the ventral sheet member in which the waist elastic members are present and the crotch sheet member overlap each other, opposite side edges extending in the longitudinal direction on both sides of the crotch sheet member are parallel to each other at least when the disposable diaper is flatly developed, and an apparent width of the crotch sheet member as measured in the transverse direction after the waist elastic members have been left contract and thereby the crotch sheet member has been left shrink together with the ventral sheet member and the dorsal sheet member is larger on a border line with the dorsal sheet member than on a border line with the ventral sheet member.

The expression "the disposable diaper is flatly developed" used herein means that the ventral sheet member, the dorsal sheet member and the crotch sheet member are developed and flattened against the elastic force of the waist elastic members or the other elastic members. The expression "leave the various members contract" used herein means that the waist elastic members bonded under tension to the diaper are freely left contract in the absence of any external force exerted on the diaper until equilibrium with a drag from the materials constituting the ventral and dorsal sheet members is attained.

According to one preferred embodiment of the present invention on the second aspect thereof, the crotch sheet member is provided along the opposite side edges of the crotch sheet member with elastic members bonded thereto under tension and, in addition, provided with the body fluid absorbent structure spaced inside the opposite side edges of the crotch sheet member so as to be symmetric about the longitudinal center line, the body fluid absorbent structure has a pair of longitudinal sides extending in parallel to the opposite side edges of the crotch sheet member, the opposite longitudinal sides curve inwardly of the body fluid absorbent structure to form curved segments symmetrically about the longitudinal center line, and the curved segments lie on the side of the ventral sheet member as viewed in the longitudinal direction.

According to another preferred embodiment, the waist elastic members exhibit at least along the segments thereof extending across the body fluid absorbent structure on the side of the ventral sheet member a tensile stress higher on the side of the ventral sheet member than on the side of the dorsal sheet member in the disposable diaper flatly developed.

According to still another preferred embodiment, the ventral sheet member and the dorsal sheet member are provided with the waist elastic members bonded under tension thereto so that the waist elastic members extending across the body fluid absorbent structure on the side of the ventral sheet member are arranged at the intervals closer than the intervals of the waist elastic members extending across the body fluid absorbent structure on the side of the dorsal sheet member.

According to yet another preferred embodiment, the waist elastic members extending across the dorsal sheet member exhibit at least in the vicinity of the border line between the dorsal sheet member and the crotch sheet member exhibit an elasticity lower than an elasticity exhibited by these waist elastic members in the remaining region.

According to further another preferred embodiment, the disposable diaper has been shaped in pants by joining the opposite side edges extending in the longitudinal direction on both sides of the ventral sheet member to the opposite side edges extending in the longitudinal direction on both sides of the dorsal sheet member so that these ventral and dorsal sheet members are annularly joined to each other to define a waist-opening while the ventral and dorsal sheet members annularly joined in this manner cooperate with the crotch sheet member joined to these ventral and dorsal sheet members to define a pair of leg-openings.

On the third aspect of the present invention, the object set forth above is achieved by an improvement in the absorbent article comprising a height direction, a longitudinal direction and a circumferential direction and comprising belt members annularly defining a front waist region and a rear waist region in the circumferential direction and a liquid-absorbent structure defining a crotch region extending between the front and rear waist regions wherein the belt members are provided with waist contractile means biasing the belt members to shrink in the circumferential direction.

The improvement according to the third aspect of the present invention is characterized in that the liquid-absorbent structure has first and second ends opposed to and spaced from each other in the longitudinal direction wherein an outer surface of the first end overlaps an inner surface of the front belt section in the front waist region to define a first overlapping region and an outer surface of the second end overlaps an inner surface of the belt section in the rear waist region to define a second overlapping region, the waist contractile means extend partially across at least one of the first overlapping region and the second overlapping region, and the liquid-absorbent structure is joined to the belt members at least in the first overlapping region or the second overlapping regions by means of joint zones extending in the height direction and arranged intermittently in the circumferential direction and a first joint-free zones defined between each pair of the adjacent joint zones define vent channels allowing the crotch region to fluid-communicate with the front and rear waist regions.

According to one preferred embodiment, the vent channels comprise first vent channels defined between the inner surface of the liquid-absorbent structure and the article wearer's skin and second vent channels defined between the outer surface of the liquid-absorbent structure and the inner surface of the belt members.

According to another preferred embodiment, the first and second overlapping regions respectively have upper and lower ends opposed to and spaced from each other in the longitudinal direction and side edges opposed to and spaced from each other in the circumferential direction, and second joint-free zones are defined along at least one of the upper and lower ends.

According to still another preferred embodiment, the joint zones comprise continuous joint zones extending in the longitudinal direction and intermittent joint zones divided in two segments in the longitudinal direction.

According to yet another preferred embodiment, the continuous joint zones are formed in the vicinity of the side edges of the first and second overlapping regions and the intermittent joint zones are arranged between the continuous joint zone formed in the vicinity of one of the side edges and the continuous joint zone formed in the vicinity of the other side edge.

According to further another preferred embodiment, the intermittent joint zones are formed in the vicinity of the side edges of the first and second overlapping regions and the continuous joint zones are arranged between the intermittent joint zone formed in the vicinity of one of the side edges and the intermittent joint zone formed in the vicinity of the other side edge.

According to an alternatively preferred embodiment, the belt members are provided with a plurality of vent holes extending through the belt members in a thickness direction thereof.

According to another alternatively preferred embodiment, the liquid-absorbent structure comprises a topsheet facing the article wearer's skin, a backsheet facing the article wearer's clothes, a liquid-absorbent core sandwiched between these sheets and cover sheets adapted to cover at least one of the first and second ends wherein said cover sheets present ventilation rate of $0.15 \text{ kPa·S/m}^2$ or less.

Effect of the Invention

With respect to the first aspect of the present invention, the reinforcing means provided between halves of a fibrous nonwoven fabric folded in two so as to extend along the peripheral edge of the waist-opening serves to reinforce the peripheral edge of the waist-opening so that the diaper may be protected against tearing even if the peripheral edge of the waist-opening repeats stretch and contraction.

With respect to the second aspect of the present invention, the apparent transverse dimension of the crotch sheet member as measured after the waist elastic members have been left contract and thereby the crotch sheet member has been left shrink together with the ventral sheet member and the dorsal sheet member is larger along the border line with the dorsal sheet member than along the border line with the ventral sheet member. In other words, the apparent width of the crotch sheet member is sufficiently larger in the dorsal side than in the ventral side to ensure that the wearer's buttocks can be reliably covered with this dorsal section.

Furthermore, the apparent transverse dimension of the crotch sheet member is relatively small and therefore it is unlikely that the crotch sheet member might become bulky in the wearer's crotch region and the wearer might experience a discomfort feeling to wear the diaper. In addition, the apparent transverse dimension of the crotch sheet member gradually decreases from the dorsal side toward the ventral side. This feature also leads to an advantageous effect. Specifically, a pair of the leg-openings defined by cooperation of the crotch sheet member with the annularly joined ventral and dorsal sheet members is biased to open rather forwardly of the diaper. These features allow the present invention to provide the three piece-type disposable diaper with the improved a fit of the diaper to the wearer particularly in the region extending from the wearer's buttocks toward the wearer's legs.

With respect to the third aspect of the present invention, the belt members are respectively provided with the waist contractile means biasing the belt members to shrink in the circumferential direction and the liquid-absorbent structure is joined to the belt members in the first and second overlapping regions by means of the joint zones extending in the height direction and arranged intermittently in the circumferential direction. In the joint-free zones each defined between the adjacent joint zones, there are formed the vent channels adapted to fluid-communicate the crotch region with the front and rear waist regions. The amount of vapor generated in the crotch region is guided via these vent channels to the exterior of the absorbent article and thereby feeling of wetness experienced by the article wearer can be effectively alleviated.

BRIEF DESCRIPTION OF THE DRAWINGS

FIG. 10 schematically shows the diaper having been shaped in pants as viewed from the ventral side.

FIG. 11 schematically shows the diaper having been shaped in pants as viewed from the dorsal side.

FIG. 12 is a plan view showing the diaper according to the second embodiment of the invention on the second aspect thereof as flatly developed.

FIG. 18 is a scale-enlarged sectional view taken along a line XVIII-XVIII of FIG. 16 with the waist contractile means being in a stretched state A and with the waist contractile means left contract.

FIG. 25 is a plan view of the diaper according to the fourth embodiment as flatly developed.

Figure 1:
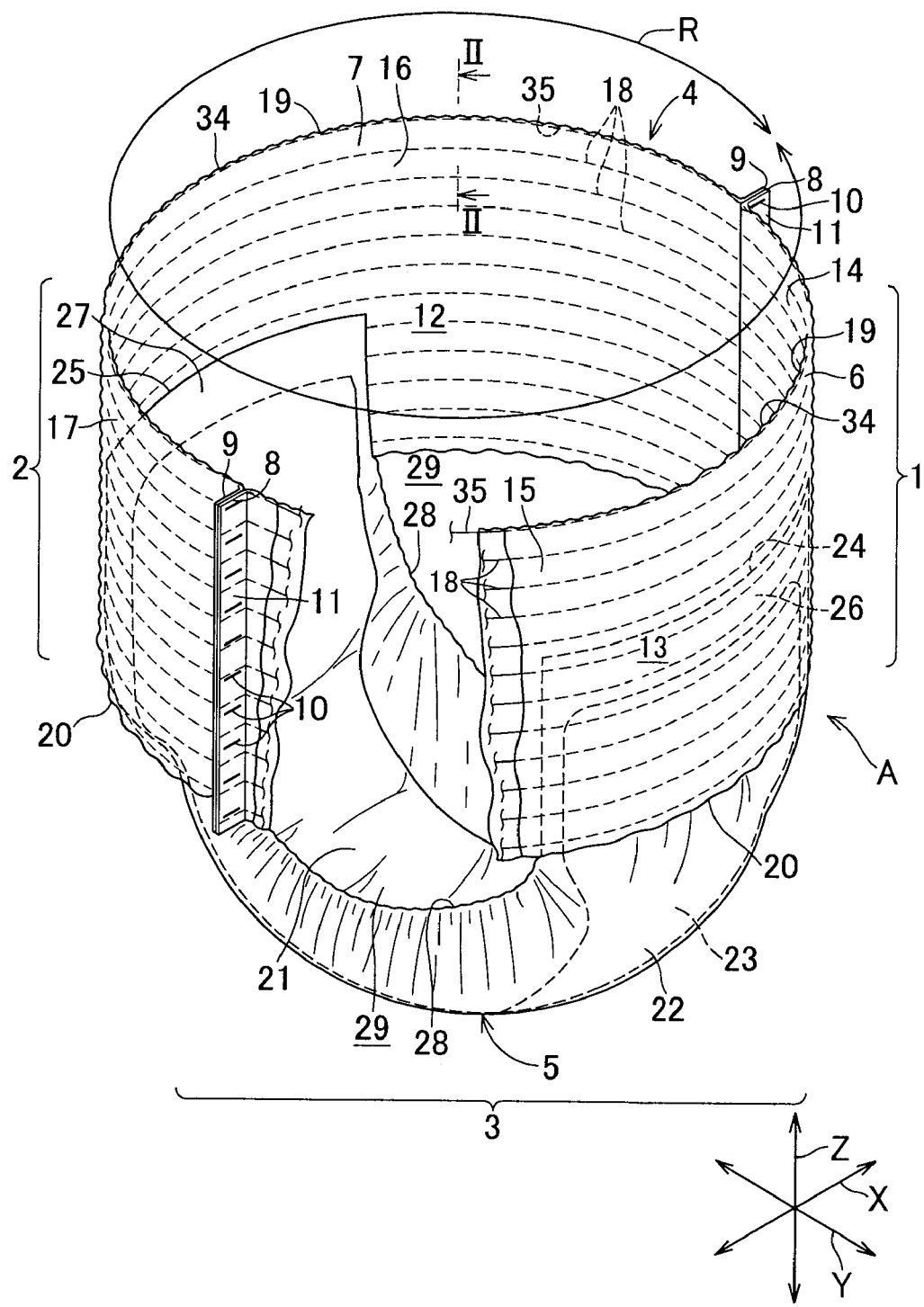
FIG. 1 is a perspective view showing a first embodiment of the present invention on a first aspect thereof.

| IDENTIFICATION OF REFERENCE NUMERALS USED IN THE DRAWINGS | |
|---|---|
| A | chassis |
| 1 | front waist region |
| 2 | rear waist region |
| 3 | crotch region |
| 12 | inner side facing wearer's skin |
| 13 | outer side facing wearer's clothes |
| 19 | peripheral edge of waist-opening |
| 34 | fold line |
| 35 | reinforcing elastic member (reinforcing means) |
| 201 | disposable diaper |
| 202 | ventral sheet member |
| 203 | dorsal sheet member |
| 204 | crotch sheet member |
| 205 | body fluid absorbent structure |
| 206 | waist elastic members |
| 207 | waist-opening |
| 208 | leg-openings |
| 221 | opposite side edges of ventral region |
| 222 | opposite side edges of dorsal region |
| 241 | opposite side edges of crotch region |
| 242 | elastic members for crotch region |
| 251 | opposite side edge |
| 252 | curved segments |
| 301 | front waist region |
| 302 | rear waist region |
| 303 | crotch region |
| 304 | belt member |
| 305 | liquid-absorbent structure |
| 312 | inner side facing wearer's skin |
| 313 | outer side facing wearer's clothes |
| 318 | waist elastic members (waist contractile means) |
| 324 | first end |
| 325 | second end |
| 326 | first overlapping region |
| 327 | second overlapping region |
| 332 | joint zones |
| 334 | first vent channels |
| 335 | second vent channels |
| 345 | first joint-free zones |
| 346, 347 | second joint-freezones |
| 348 | continuous joint zones |
| 349 | intermittent joint zones |

DESCRIPTION OF THE BEST MODE FOR WORKING OF THE INVENTION

First Aspect of the Invention

Figure 2:
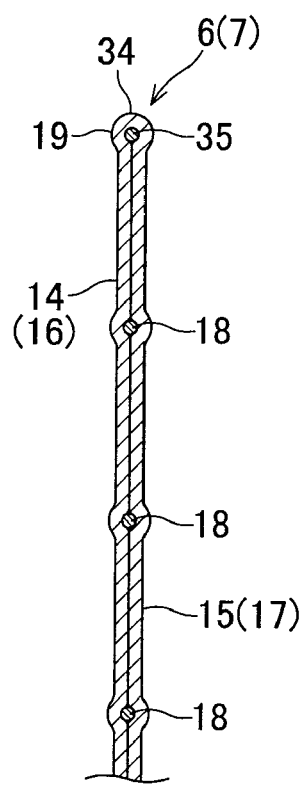
FIG. 2 is a sectional view taken along the line II-II in FIG. 1.
Figure 3:
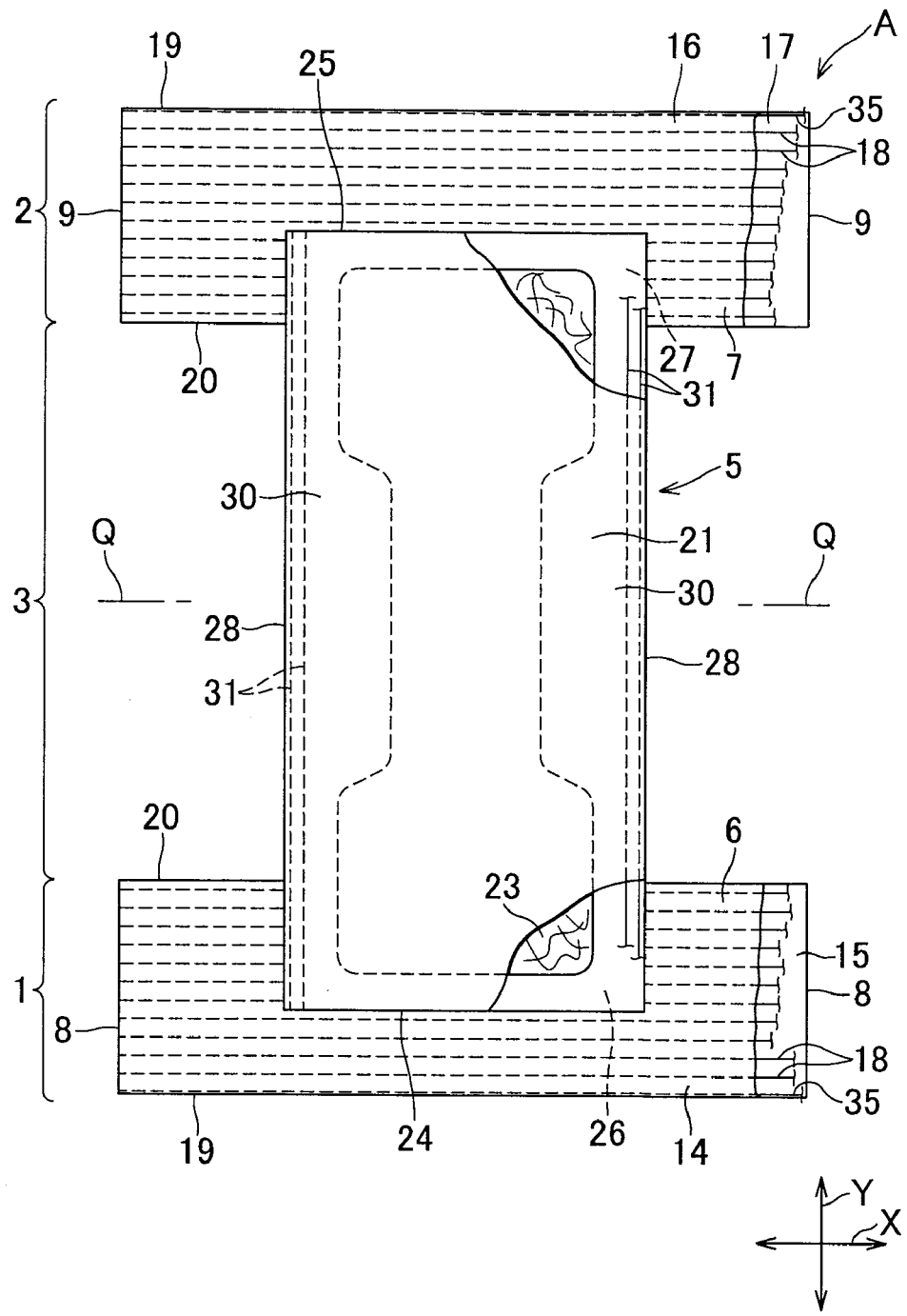
FIG. 3 is a plan view of the diaper shown in FIG. 1 as developed and flattened.

FIGS. 1 through 3 illustrates a disposable diaper as a first embodiment of the absorbent article according to the present invention wherein FIG. 1 is shows the diaper as put on the wearer as partially cutaway for convenience of illustration. As shown, a chassis A comprises a belt member 4 defining a front waist region 1 and a rear waist region 2 which are jointed together to form an annulus extending in a circumferential direction R and a liquid-absorbent structure 5 defining a crotch region 3 extending between the front and rear waist regions 1, 2.

The belt member 4 are composed of a front belt section 6 defining the front waist region 1 and a rear belt section 7 defining the rear waist region 2. A pair of side edges 8, 8 of the front belt section 6 opposite in the circumferential direction R and a pair of side edges 9, 9 of the rear belt section 7 opposite in the circumferential direction R are put flat and jointed together, respectively, along a pair of seams 11 respectively comprising a plurality of side edge joints 10 arranged intermittently in a height direction Z. The front and rear belt sections 6, 7 are joined to each other at the respective side edge joints 10 to define a waist-opening.

The front belt section 6 comprises an inner sheet 14 defining an inner side 12 facing the wearer's skin and an outer sheet 15 defining an outer side 13 facing the wearer's garment while the rear belt section 7 comprises an inner sheet 16 defining the inner side 12 and an outer sheet 17 defining the outer side 13 facing the wearer's garment. The inner and outer sheets 14, 15 of the front belt section 6 as well as the inner and outer sheets 16, 17 of the rear belt section 7 are respectively formed by folding a single fibrous nonwoven fabric in two along a fold line 34. The fibrous nonwoven fabric before being folded in two to form the inner and outer sheets 14, 15 or the inner and outer sheets 16, 17 has a total light transmittance of about 80% or higher. The inner and outer sheets 14, 15 as well as 16, 17 formed by folding the fibrous nonwoven fabric in two and put flat together has a total light transmittance of about 66% or higher, allowing the wearer's skin to be seen through these inner and outer sheets 14, 15 or 16, 17. Measurement result of such total light transmittance is shown by TABLE 1.

TABLE 1

| (%) | A | B | C | D |
|---|---|---|---|---|
| Total light transmittance through a single sheet layer | 83.51 | 80.33 | 85.40 | 88.41 |
| Total light transmittance through two sheet layers | 68.14 | 66.43 | 73.06 | 76.10 |

TABLE 1 designates types of the fibrous nonwoven fabric used for the inner and outer sheets 14, 15 and 16, 17 by A, B, C and D, respectively, and shows mean values of the total light transmittance exhibited by the respective types of the fibrous nonwoven fabric before and after folded in two. Measurement was carried out using five samples (N=5) for each type of the fibrous nonwoven fabric. The types of the fibrous nonwoven fabric may be selected from the group conventionally well known in the field of the diaper such as spun bond-, melt blown-, point bond- and air-through-types. The inner and outer sheets 14, 15 are formed by folding one and same type of a fibrous nonwoven fabric in two and this is true for the inner and outer sheets 16, 17. For the front and rear belt sections 6, 7, one and same type of a fibrous nonwoven fabric is used and, in this manner, all of the inner and outer sheets 14, 15, 16, 17 may typically be formed by one and same type of a fibrous nonwoven fabric.

The total light transmittance was measured in accordance with JIS-K7105 and, more specifically, the samples each having a width of about 50 mm and a length of about 40 mm were obtained and the flicker photometer type colorimeter Z-300A (available from Nippon Denshoku Industries Co., Ltd.) was used in a manner that each of the samples was held by a turbidimeter to measure a turbidity.

An uppermost peripheral edge 19 of the waist-opening as viewed in the height direction Z defined by the fold line 34 along which the fibrous nonwoven fabric has been folded in two, i.e., the inner and outer sheets 14, 15 and 16, 17, contains therein a string-like reinforcing elastic member 35 functioning as reinforcing means. The reinforcing elastic member 35 extends under tension in the circumferential direction R. Aside from the reinforcing elastic member 35 in the height direction Z toward the crotch region 3, i.e., downward as viewed in FIG. 1, the belt member 4 is intermittently provided with a plurality of waist elastic members 18 spaced one from another. These waist elastic members 18 are sandwiched between the inner and outer sheets 14, 15 and between the inner and outer sheets 16, 17 so as to extend under tension in the circumferential direction R. While the reinforcing elastic member 35 is similar to the waist elastic members 18 in its material and configuration, this elastic member 35 is referred to as the reinforcing elastic member 35 taking account of its placement along the peripheral edge 19 of the waist-opening. These elastic members 18 inclusively of the reinforcing elastic member 35 are bonded under tension to at least one of the inner and outer sheets 14, 15 or at least one of the inner and outer sheets 16, 17 by means of adhesive (not shown).

FIG. 2 is a sectional view taken along the line II-II in FIG. 1 showing, in an enlarged scale, the peripheral edge 19 of the waist-opening provided with the reinforcing elastic member 35. While FIG. 2 relates only to the inner and outer sheets 14, 15 for convenience of illustration, the inner and outer sheets 16, 17 also will be discussed with reference to FIG. 2 since the latter is substantially the same as the former. As shown, the reinforcing elastic member 35 extends along the peripheral edge 19 of the waist-opening inside the fold line 34 along which the inner and outer sheets 14, 15 and the inner and outer sheets 16, 17 are folded. Specifically, the reinforcing elastic member 35 is in tight contact with the inner and outer sheets 14, 15 as well as with the inner and outer sheets 16, 17 defining the peripheral edge 19 of the waist-opening without leaving any substantial clearance gap between the reinforcing elastic member 35 and the fold line 34. Provision of the reinforcing elastic member 35 along the peripheral edge 19 defined by the front and rear belt sections 6, 7 allows the fibrous nonwoven fabric to have a tensile strength and a tear strength reinforced along the peripheral edge 19 of the waist-opening and thereby reduces a possibility that the fibrous nonwoven fabric might be easily broken along this peripheral edge 19. In addition, the reinforcing elastic member 35 facilitates the fibrous nonwoven fabric to be folded in two, i.e., the inner and outer sheets 14, 15 and the inner and outer sheets 16, 17.

If the reinforcing elastic member 35 is provided so as to be spaced from the peripheral edge 19 of the waist-opening, i.e., below the peripheral edge 19 as viewed in FIG. 1, a section of the sheets defined between the peripheral edge 19 of the waist-opening and the reinforcing elastic member 35 will form a frill extending out of the circumferential direction R. Such frill may be bothersome to the eye and irritate the wearer's skin. In contrast with this, the embodiment of the invention described here is free from a possibility of forming any frill, so the article is neat to the eye and able to protect the wearer's skin from undesired irritation.

A distance from the reinforcing elastic member 35 to the waist elastic member 18 adjacent thereto in the height direction Z as well as a distance between each pair of the adjacent waist elastic members 18 may be in a range of about 8 to about 10 mm and stretch ratio of the reinforcing elastic member 35 and the waist elastic members 18 may be set to a range of 1.5 to 3.0.

The belt member 4 provided with the reinforcing elastic member 35 and the waist elastic members 18 is combined with the absorbent structure 5 to form the chassis A shown by FIG. 1. Referring to FIG. 1, the absorbent structure 5 comprises a liquid-pervious topsheet 21 defining the inner side 12 facing the wearer's skin, a liquid-impervious backsheet 22 defining the outer side 13 facing the wearer's garment and a liquid-absorbent core 23 wrapped with tissue paper or the like (not shown) wherein the liquid-absorbent core 23 is permanently bonded to at least one of the topsheet 21 and the backsheet 22. A moisture-pervious but liquid-impervious film may be used as the backsheet 22 and, in this case, a fibrous nonwoven fabric obtained by spun bond-, through-air-processes or the like may be laminated on such film to improve a feeling to wear.

The liquid-absorbent structure 5 extends across the crotch region 3 in a longitudinal direction Y and includes a first end portion 24 and a second end portion 25 opposed to and spaced from each other in the longitudinal direction Y. The liquid-impervious backsheet 22 of the first end portion 24 is bonded to the inner sheet 14 of the front belt section 6 so that a first joint region 26 may be defined by a region in which the liquid-absorbent structure 5 overlaps the front belt section 6. The liquid-impervious backsheet 22 of the second end portion 25 is bonded to the inner sheet 16 of the rear belt section 7 so that a second joint region 27 may be defined by a region in which the liquid-absorbent structure 5 overlaps the rear belt section 7. A sub-region of the front waist region 1 except the first joint region 26 and a sub-region of the rear waist region 2 except the second joint region 27 define see-through regions allowing the wearer's skin to be seen through the diaper.

The front and rear belt sections 6, 7 are joined to the liquid-absorbent structure 5 so that respective lower ends 20 of the front and rear belt sections 6, 7 opening toward the crotch region cooperate with a pair of side edges 28 of the liquid-absorbent structure 5 extending in the longitudinal direction Y to a pair of leg-openings 29.

FIG. 3 is a plan view of the diaper developed in the longitudinal direction Y after the respective side edge joints 10 have been broken. In FIG. 3, all of the reinforcing elastic member 35, the waist elastic members 18 and the elastic members 31 provided along the side edges of the crotch region remain under tension and not biased to contract.

As will be apparent from FIG. 3, both the topsheet 21 and the backsheet 22 are substantially rectangular while the liquid-absorbent core 23 is substantially hourglass-shaped. In other words, the liquid-absorbent core 23 has its dimension in the transverse direction X gradually reduced toward a transverse center line Q bisecting a width of the core 23 so that a dimension of the core 23 is smaller in the vicinity of the transverse center line Q than in the first end portion 24 and the second end portion 25.

Along the opposite side edges 28 of the liquid-absorbent structure 5, the top- and backsheets 21, 22 extend outward beyond the liquid-absorbent core 23 to form a pair of opposite side flaps 30 each having an area enlarged in the vicinity of the transverse center line Q since the liquid-absorbent core 23 is hourglass-shaped. Between the top- and backsheets 21, 22, the elastic members 31 for the crotch region are attached under tension so as to extend in the longitudinal direction Y along the opposite side edges 28. Under contraction of these elastic members 31 for the crotch region, the opposite side edges 28 are put in tight contact around the wearer's legs and thereby the side flaps 30 prevent body waste such as urine from leaking from otherwise left gaps between the wearer's legs and the leg-openings 29 (See FIG. 1).

Of the first and second joint regions 26, 27 in which the front and rear belt sections 6, 7 overlap the liquid-absorbent structure 5, the second joint region 27 has an area smaller than an area of the first joint region 26. Obviously the wearer's skin can not be seen through the liquid-absorbent structure 5 since the liquid-absorbent structure 5 contains therein the liquid-absorbent core 23 and, smaller the areas of the first and second joint regions 26, 27, larger the region in which the wearer's skin can be seen through the diaper. Usually, the wearer's dorsal region including the buttock to be covered with the rear waist region 2 is more prone to stuffiness and/or heat rash than the ventral region to be covered with the front waist region 1, the rear waist region 2. In view of this, the diaper according to the present embodiment is constructed so that the see-through region may have an area larger in the rear waist region 2 than in the front waist region 1 and the air-permeability may be higher in the rear waist region 2 than in the front waist region 1.

The first joint region 26 and the second joint region 27 are dimensioned to have respective areas corresponding to about 25% of the areas occupied by the front and rear belt sections 6, 7, respectively. In other words, the respective see-through regions defined by the sub-regions other than the joint regions are mentioned to have respective areas corresponding to about 75% of the areas occupied by the front and rear waist regions 1, 2. However, it should be understood that the see-through regions may be dimensioned to have the areas corresponding to at least about 40% or more of the front and rear waist regions 1, 2 to achieve the desired effect. The areas of the respective see-through regions were measured with the diaper developed as seen in FIG. 3. Specifically, the areas of the respective see-through regions were measured with the reinforcing elastic member 35, the waist elastic members 18 and the elastic members 31 for the crotch region being held under tension or before these elastic members are attached to the diaper. The areas of the front and rear belt sections 6, 7 as well as the areas of the first and second joint regions 26, 27 were also measured on the same condition as for the see-through regions. It should be noted that the opposite side edges allotted to form a pair of the seams 11 were left out from the measurement.

The first and second joint regions 26, 27 are formed substantially in respective middles of the first and second belt sections 6, 7 as viewed in the transverse direction X so that the liquid-absorbent structure 5 is not joined to the front and rear belt sections 6, 7 at the lateral portions thereof as viewed in the transverse direction X including the opposite side edges 8, 9. In consequence, the see-through regions in which the liquid-absorbent structure 5 is absent are defined in the form of two opposite square U-shaped regions opening in the transverse direction X. Thus, one of the see-through regions extends from the first end portion 24 of the liquid-absorbent structure 5 outward in the longitudinal direction Y and the other extends from the second end portion 25 outward in the longitudinal direction Y. In this way, the wearer's skin can be seen through the diaper put on the wearer's body around the wearer's waist inclusively of opposite lateral regions, ventral region and dorsal region.

Using the diaper as has been described above, a survey in the form of questionnaire was conducted with respect to an air-permeability and a cool feeling to the eye. While the inner and outer sheets 14, 15 and 16, 17 having a total light transmittance of about 66% have been described with reference to TABLE 1, a desired see-through effect was obtained also by the sheets having a total light transmittance of about 55% or higher. Taking account of this, the diaper according to this first embodiment having a total light transmittance of about 55% or higher and the diaper having a total light transmittance less than about 55% were tried on babies and sent out questionnaires to parents "Stuffiness-free to the eye?" and "Cool to the eye?". Answers from the parents are indicated by TABLE 2. With respect to the questionnaire "Stuffiness-free to the eye?", answers were obtained from ten (10) parents and with respect to the questionnaire "Cool to the eye?", answers were obtained from thirteen (13) parents.

TABLE 2

|  | Diaper having light transmittance less than 55% | Diaper according to the invention |
| --- | --- | --- |
| (1) Stuffiness-free to the eye? | | |
| Stuffiness-free at all to the eye | 0 | 3 |
| Stuffiness-free to the eye | 1 | 6 |
| Neutral to the eye | 1 | 1 |
| Not stuffiness-free to the eye | 5 | 0 |
| Not stuffiness-free at all to the eye | 5 | 0 |
| (2) Cool to the eye? | | |
| Very cool to the eye | 0 | 4 |
| Cool to the eye | 3 | 6 |
| Neutral to the eye | 2 | 3 |
| Not cool to the eye | 6 | 0 |
| Not cool at all to the eye | 2 | 0 |

As will be apparent from TABLE 2, to the questionnaire "Stuffiness-free to the eye?" with respect to the diaper having a total light transmittance less than about 55%, one (1) parent answered "Stuffiness-free to the eye" and totally eight (8) parents answered "Not stuffiness-free to the eye" and "Not stuffiness-free at all to the eye". With respect to the diaper according to this first embodiment of the invention, totally nine (9) parents answered "Stuffiness-free at all to the eye" and "Stuffiness-free to the eye" and none of parents answered "Not stuffiness-free to the eye" or "Not stuffiness-free at all to the eye". To the questionnaire "Cool to the eye?" with respect to the diaper having a total light transmittance less than about 55%, three (3) parents answered "Cool to the eye" and totally eight (8) patents answered "Not cool to the eye" or (Not cool at all to the eye". With respect to the diaper according to this first embodiment of the invention, ten (10) parents answered "Very cool to the eye" and "Cool to the eye" and none of the parents answered "Not cool to the eye" or "Not cool at all to the eye". As apparent from such result of questionnaire survey, about 90% of the parents were in positive response to the diaper according to this first embodiment of the invention with respect to the stuffiness-free property to the eye and about 77% of the parents were in positive response to the diaper according to this first embodiment of the invention with respect to the coolness to the eye.

The result of the questionnaires indicated in TABLE 2 demonstrated that the diaper which is stuffiness-free and cool at least to the eye can be provided by improving a total light transmittance to a level of about 55%. However, such improvement of the total light transmittance of the fibrous nonwoven fabric often results in decreasing the fineness as well as the basis weight thereof and, consequently, the fibrous nonwoven fabric will be correspondingly prone to tear. According to this first embodiment of the invention, such problem is solved by providing the peripheral edge 19 of the waist-opening which would otherwise be most prone to tear with the reinforcing elastic member 35 so that the fibrous nonwoven fabric may be reinforced along the peripheral edge 19 of the waist-opening and protected from readily tearing. In addition to the reinforcing elastic member 35, the front and rear waist regions 1, 2 are provided with a plurality of the waist elastic members 18 so that the inner and outer sheets 14, 15, 16, 17 of the front and rear waist regions 1, 2 are reinforced by these waist elastic members 18. The reinforcing elastic member 35 is substantially the same as the waist elastic member 18 in material as well as in configuration and therefore a cost for separate preparation of the reinforcing elastic member 35 can be saved and, in addition, it is not required to increase the number of steps for production since the reinforcing elastic member 35 and the waist elastic members 18 may be attached to the diaper at the same time.

The reinforcing elastic member 35 as the reinforcing means may be replaced by an elasticized sheet or an inelastic fibrous nonwoven fabric without departing from the scope of the invention. Use of the elastic member or the elasticized sheet as the reinforcing means allows the belt member 4 defining the front and rear waist regions 1, 2 to contract in the circumferential direction R and thereby to prevent body waste from leaking beyond the waist-opening.

While this first embodiment in the form of a so-called pants-type diaper is described here, it will be apparent for those skilled in the art that an arrangement of this first embodiment applicable also to an open-type diaper. While the belt member 4 defining the front and rear waist regions 1, 2 and the liquid-absorbent structure 5 defining the crotch region 3 have been described to be separately prepared and then to be assembled together, it is possible to form the front and rear waist regions and the crotch region from the same member. For example, it is possible to form the front and rear waist regions and the crotch regions by the inner and outer sheets and then to place the liquid-absorbent structure on the wearer's skin facing side of the inner sheet or to sandwich the liquid-absorbent structure between the inner and outer sheets. In any case, the see-through regions for the wearer's skin preferably occupy at least about 40% or more of the front and rear waist regions. While the front and rear waist regions are defined by the front and rear belt sections 6, 7, respectively, according to this embodiment, it is possible for the other pants-type or open-type diaper to define regions extending from the peripheral edge of the waist-opening downward by about 27% in the longitudinal direction as the front and rear waist regions, respectively.

While the inner and outer sheets have been described to be formed by folding a single fibrous nonwoven fabric in two, it is possible to bond separate sheets to each other to form the inner and outer sheets. In any case, these inner and outer sheets may be provided along the peripheral edge of the waist-opening with the reinforcing means to assure a desired strength of the fibrous nonwoven fabric. While the inner and outer sheets preferably comprise a liquid-absorbent fibrous nonwoven fabric, it is not essential for the fibrous nonwoven fabric to have liquid-absorbent property.

While the single sheet of a fibrous nonwoven fabric before folded upon itself to form the inner and outer sheets 14, 15, 16, 17 has a total light transmittance of about 80% or higher according to this first embodiment, the lower limit total light transmittance of about 55% or higher for the intended see-through effect for the wearer's skin may be achieved so far as the single fibrous nonwoven fabric has a total light transmittance of about 70% or higher. While the areas of the first and second joint regions 26, 27 in which the liquid-absorbent structure 5 overlaps the front and rear belt sections 6, 7, respectively, are about 25% of the front and rear waist regions 1, 2, respectively, according to the first embodiment, the areas of the first and second joint regions 26, 27 are not limited to such value and preferably in a range of about 15% to about 30%.

The first and second joint regions 26, 27 may extend to the peripheral edge 19 of the waist-opening. In other words, the liquid-absorbent structure 5 may be attached to the belt member 4 so as to extend from the front peripheral edge 19 of the waist opening to the rear peripheral edge 19 of the waist opening. In this case, the area of the see-through region for the wearer's skin is reduced but the liquid-absorbent structure is correspondingly enlarged and thereby a preventive effect against leak of body waste is enhanced.

Figure 4:
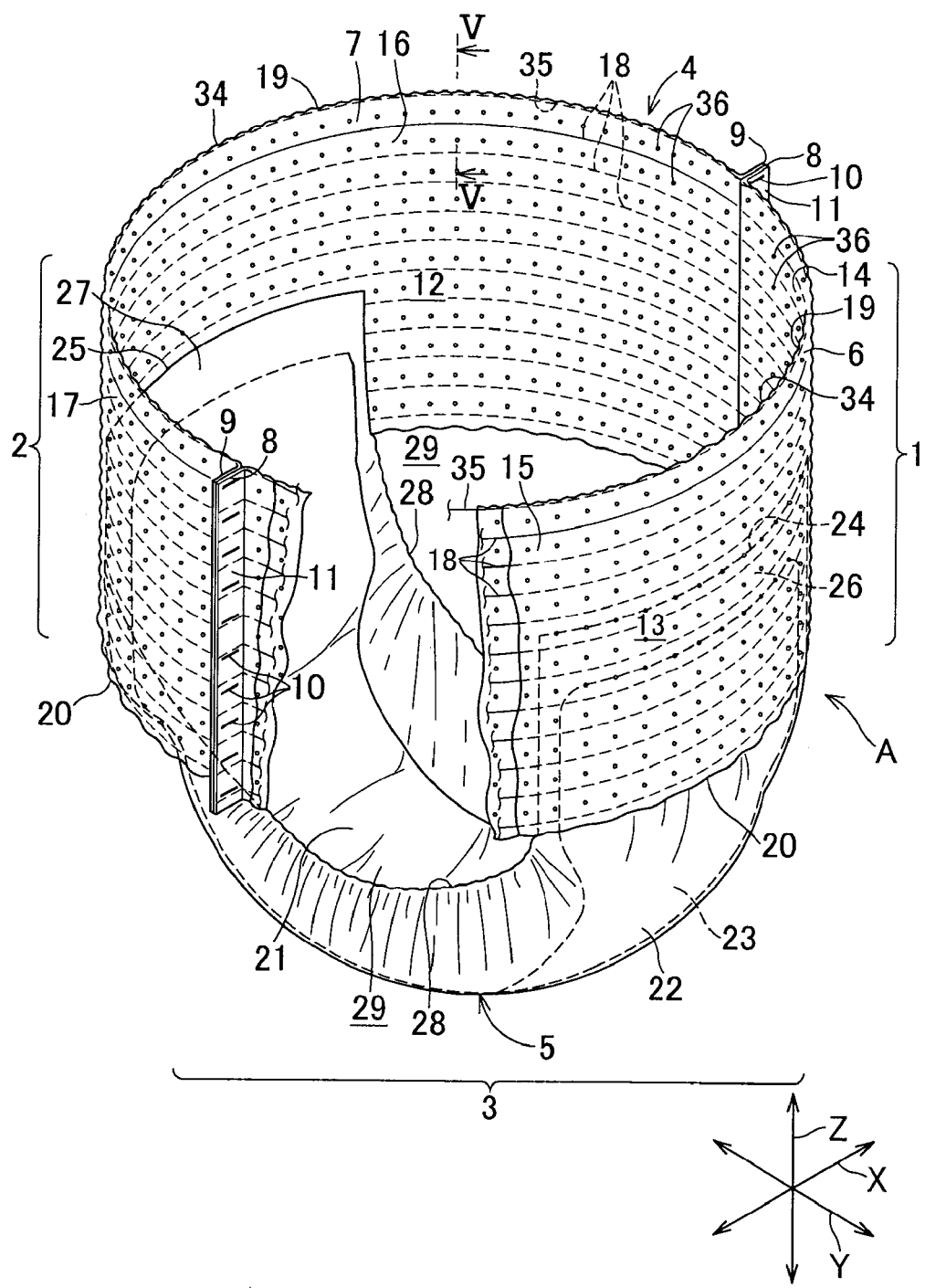
FIG. 4 is a perspective view showing a second embodiment of the present invention on the first aspect thereof.

FIG. 4 shows a second embodiment of the present invention wherein the inner and outer sheets 14, 15 as well as the inner and outer sheets 16, 17 are provided with a plurality of through-holes 36 extending through these sheets in a thickness direction of the diaper. The other features are similar to those in the first embodiment and details thereof will not be described. The through-holes 36 each having a diameter of 1 to about 2 mm are distributed over the entire ranges of the inner and outer sheets 14, 15 and the inner and outer sheets 16, 17. These through-holes 36 are arranged at regular intervals of about 8 to about 10 mm in the longitudinal direction Y and at regular intervals of about 5 to about 20 mm in the transverse direction X.

Figure 5:
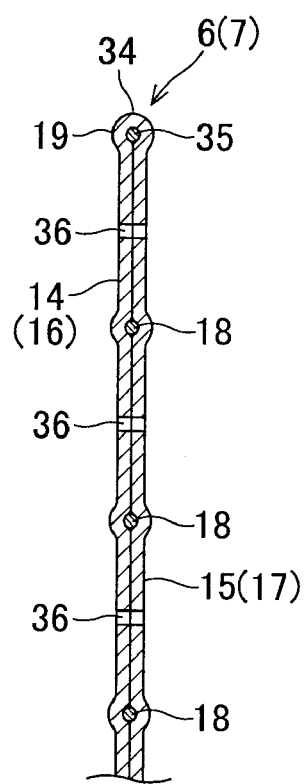
FIG. 5 is a sectional view taken along the line V-V in FIG. 2.

FIG. 5 is a sectional view taken along the line V-V in FIG. 4. As shown, the through-holes 36 extend through the inner and outer sheets 14, 15 as well as the inner and outer sheets 16, 17 in the thickness direction of the diaper. The through-holes 36 are formed between the reinforcing elastic member 35 and the adjacent waist elastic member 18 and between each pair of the adjacent waist elastic members 18.

Formation of these through-holes 36 allows the wearer's skin to be visually recognized through these through-holes 36. The inner and outer sheets 14, 15, 16, 17 having a total light transmittance of about 55% or higher allows the wearer's skin to be seen through these sheets and, in addition, the through-holes 36 allow the skin to be visually recognized so that the diaper of the stuffiness-free and cool to the eye can be provided. By forming the through-holes 36 between the elastic members 18, 35, there is no anxiety that the see-through effect for the wearer's skin might be disturbed the presence of the elastic members. It should be understood that some of these through-holes 36 may be formed so as to overlap the reinforcing elastic members 35 or the waist elastic members 18.

While the through-holes 36 are distributed over the entire regions of the inner and outer sheets 14, 15, 16, 17 according to this second embodiment, it is not essential to distribute these through-holes 36 over the entire regions so far as these through-holes 36 are formed in the region in which the liquid-absorbent structure 5 is not present.

Second Aspect of the Invention

Figure 6:
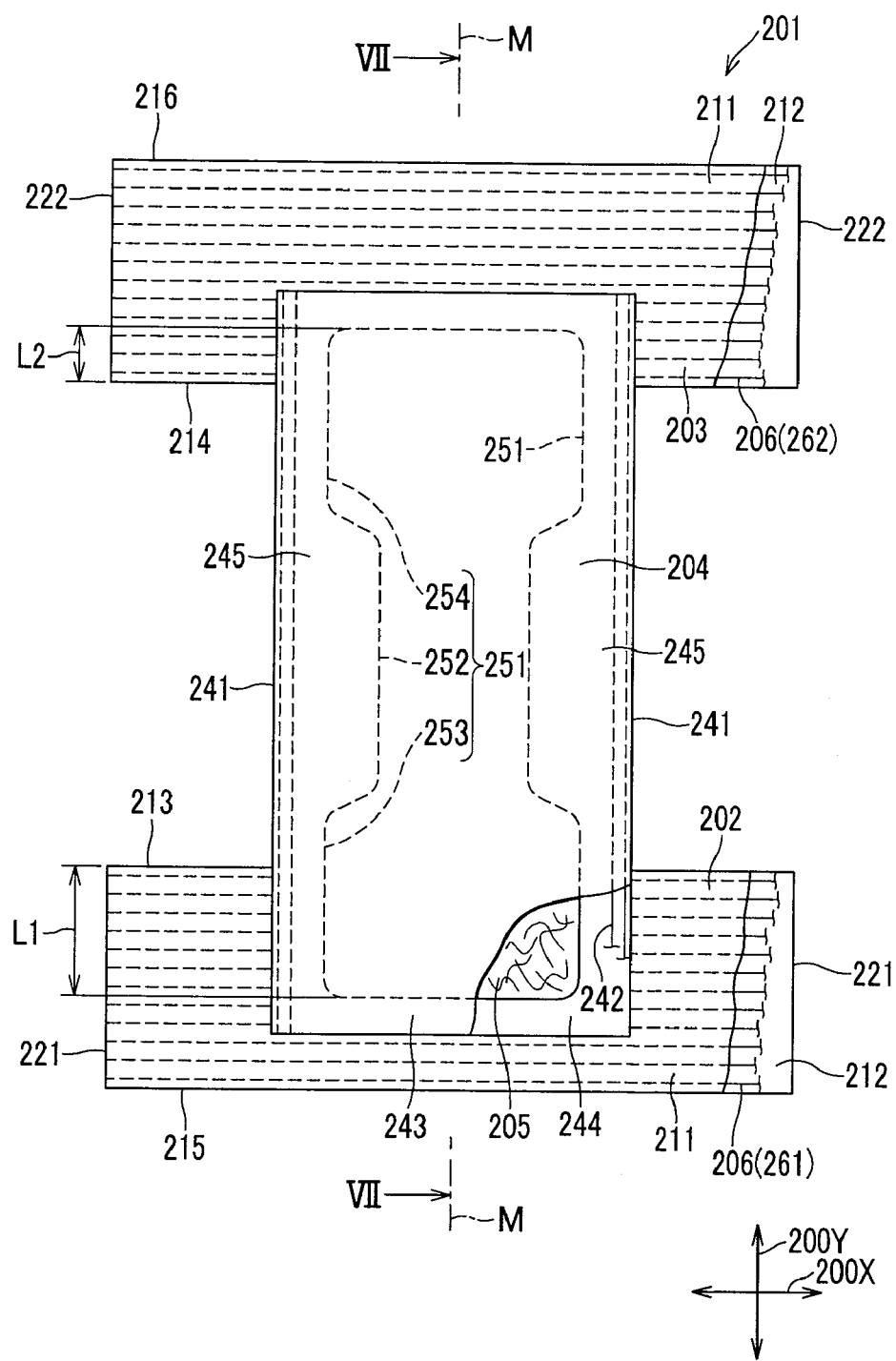
FIG. 6 is a plan view showing the diaper according to the first embodiment of the invention on a second aspect thereof as flatly developed.
Figure 7:
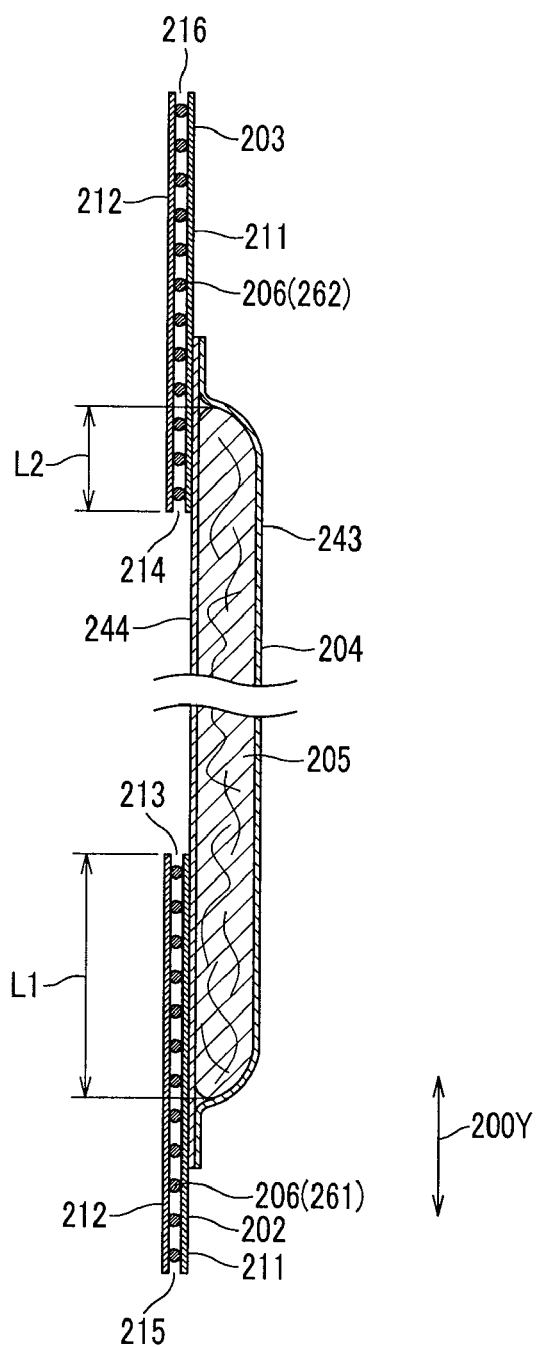
FIG. 7 is a sectional view taken along the line VII-VII in FIG. 6.
Figure 8:
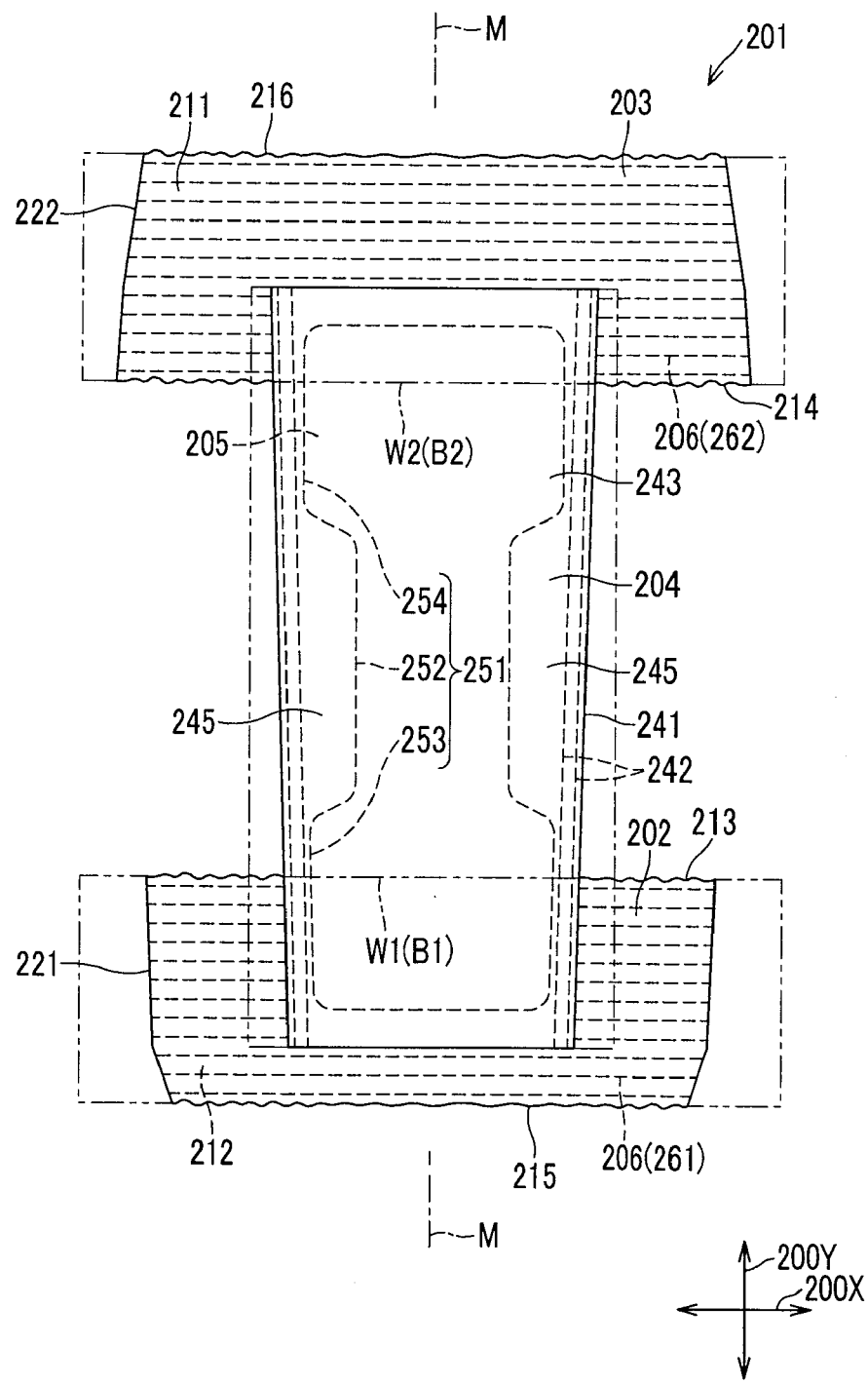
FIG. 8 is a plan view showing the diaper with the waist elastic members left contract.

Details of a diaper 201 according to the second aspect of the present invention will be described with reference to FIGS. 6 through 8. FIG. 6 is a plan view showing the diaper 201 according to the first embodiment as flatly developed, FIG. 7 is a sectional view taken along the line VII-VII in FIG. 6 and FIG. 8 is a plan view showing the diaper with the waist elastic members 206 released from the tensioned state as shown of FIG. 6.

FIG. 6 illustrates the diaper 201 as viewed from the side thereof facing the wearer's skin. The diaper 201 comprises a rectangular ventral sheet member 202 extending in a transverse direction indicated by an arrow 200X, a rectangular dorsal sheet member 203 spaced from the ventral sheet 202 and extending in parallel to the ventral sheet member 202 in the transverse direction and a rectangular crotch sheet member 204 extending in a longitudinal direction indicated by an arrow 200Y and having longitudinally opposite end portions joined to the ventral sheet member 202 and the dorsal sheet member 203, respectively approximately in middles of these ventral and dorsal sheet members 202, 203. The crotch sheet member 204 has a transverse dimension smaller than that of the ventral sheet member 202 as well as that of the dorsal sheet member 203 and includes a body fluid absorbent structure 205. The diaper 201 presents an I- or H-shape which is substantially symmetric about a longitudinal center lime M and the body fluid absorbent structure 205 is also symmetric about the longitudinal center line M.

Each of the ventral sheet member 202 and the dorsal sheet member 203 comprises air-permeable topsheet 211 and backsheet 212 sandwiching therebetween a plurality of ventral rubber strings 261 or a plurality of dorsal rubber strings 262 wherein these rubber strings 261 or 262 extend under tension in the transverse direction and intermittently affixed to the sheet members 202 or 203. The ventral rubber strings 261 are affixed to the sheet members 202 under an elongation percentage higher than an elongation percentage under which the rubber strings 262 are attached to the dorsal sheet member 203. Consequently, the ventral rubber strings 261 exhibit a stress higher than a stress exhibited by the rubber strings 262 associated with the dorsal sheet member as the diaper 201 is flatly developed. In other words, the rubber strings 261 extending across the body liquid absorbent structure 205 exhibit a stress higher than a stress exhibited by the rubber strings 262 extending across the body fluid absorbent structure 205. It should be noted here that a distance between each pair of the ventral rubber strings 261 as well as a distance between each pair of the adjacent rubber strings 262 associated with the dorsal sheet member 203 is constant. The crotch sheet member 204 is placed on the ventral sheet member 202 and the dorsal sheet member 203 so as to overlap regions of these two members 202, 203 in which the waist elastic members 206 are present. With the diaper 201 put on the wearer, the topsheet 211 faces the wearer's skin and the backsheet 212 faces away from the wearer's skin.

The rectangular crotch sheet member 204 has an area larger than an area of the body fluid absorbent structure 205 enclosed together with elastic members 242, 242 for the crotch region between a rectangular liquid-pervious sheet 243 and a liquid-impervious sheet 244. With the diaper 201 put on the wearer's body, the liquid-pervious sheet 243 faces the wearer's skin and the liquid-impervious sheet 244 faces away from the wearer's skin. With the diaper 201 flatly developed, opposite side edges 241, 241 of the crotch sheet 204 extend in parallel to each other in the longitudinal direction. Fully along these opposite side edges 241, 241 of the crotch region, the elastic members 242, 242 are intermittently bonded under tension to the crotch sheet member 204. In this first embodiment, rubber strings are used as the elastic members 242, 242 for the crotch region.

The body fluid absorbent structure 205 is joined to the crotch sheet member 204 in symmetry about the longitudinal center line M so that the body fluid absorbent structure 205 is spaced by a given distance from each of the opposite side edges 241 of the crotch region. The body fluid absorbent structure 205 overlaps both the ventral sheet member 202 and the dorsal sheet member 203 so that a longitudinal dimension L1 by which the body fluid absorbent structure 205 overlaps the ventral sheet member 202 may be larger than a longitudinal dimension L2 by which the body fluid absorbent structure 205 overlaps the dorsal sheet member 203. In this way, on the side of the ventral sheet member 202, a front section of the wearer's crotch region can be covered with the body fluid absorbent structure 205 over a sufficiently large area to absorb urine with high efficiency.

The body fluid absorbent structure 205 having opposite side edges 251 extending substantially in parallel to the opposite side edges 241 of the crotch sheet 204. The opposite side edges 251 comprise a pair of opposite segments 253 extending in parallel to each other on the side of the ventral sheet member 202, a pair of opposite segments 254 extending in parallel to each other on the side of the dorsal sheet member 203 and a pair of curved segments 252 extending in parallel to each other between the parallel segments 253 on the side of the ventral sheet member 202 and the parallel segments 254 on the side of the dorsal sheet member 203. The segments 252 are curved inwardly of the body fluid absorbent structure 205 so as to be symmetric about the longitudinal center line M of the diaper and the body fluid absorbent structure 205 as a whole presents a dumbbell-like shape. A transverse distance between the curved segments 252 is smaller than a distance between the parallel segments 253 on the side of the ventral sheet member 202 as well as than a distance between the parallel segments 254 on the dorsal sheet member 203.

A section of the body fluid absorbent structure 205 defined by the parallel segments 254 partially overlaps the dorsal sheet member 203 while a section of the body fluid absorbent structure 205 defined by the parallel segments 253 fully overlaps the ventral sheet member 202.

Sections of the liquid-pervious sheet 243 and the liquid-impervious sheet 244 extend outward in the transverse direction from the respective curved segments 252 to the opposite side edges 241 of the crotch region to form a pair of opposite side flaps 245. These side flaps 245 are provided with the elastic members 242 for the crotch region extending along the opposite side edges 241. These side flaps 245 have not the body fluid absorbent structure 205 joined thereto and have relatively low rigidity in comparison to the remaining section of the crotch region having the body fluid absorbent structure 205 joined thereto. Consequently, these side flaps 245 are easily deformed in response to stretch and contraction or the other movement of the elastic members 242 for the crotch region.

Materials for the respective sheets constituting the diaper 201 may be appropriately selected from the group of the various types of fibrous nonwoven fabrics and/or films made of thermoplastic synthetic resin conventionally used for the disposable diaper in consideration of the required properties. As the body fluid absorbent structure 205, body fluid absorbent material of well known art containing fluff pulp wrapped with tissue paper (not shown) may be used. The body fluid absorbent structure 205 contains fluff pulp and therefore exhibits a relatively high stiffness, i.e., a relatively high deformation resistance compared to the liquid-impervious sheet 244 and the liquid-pervious sheet 243. As the elastic members 242 for the crotch region and the waist elastic members 206, rubber strings, thermoplastic elastomers, taper-shaped or belt-shaped rubbers, or elasticized nonwoven fabrics or resin films may be used.

Bonding among the respective sheets, the respective elastic members, and the body fluid absorbent members constituting the diaper 201 may be carried out using the method well known in the field of disposable diapers, for example, adhesion with hot melt adhesives or heat sealings.

A tensile stress of the waist elastic members 206 generated as the diaper 201 is flat developed can be adjusted by setting an appropriate elongation percentage at which the waist elastic members 206 are attached to the diaper 201. Alternatively, the stress can be adjusted by appropriately varying material and/or sectional area of the waist elastic members 206 on the basis of one and same elongation percentage.

As shown by FIG. 7 in a sectional view, the ventral and dorsal rubber strings 261, 262 overlap the body fluid absorbent structure 205 by the intermediary of the topsheets 211 of the front and dorsal sheet members 202, 203 and the liquid-impervious sheet 244 of the crotch sheet member 204. These members constituting the diaper 201 are bonded one to another by means of hot melt adhesive (not shown) so that the body fluid absorbent structure 205 also may contract together with the ventral sheet member 202, the dorsal sheet member 203 and the crotch sheet member 204 in the transverse direction as the ventral and dorsal rubber strings 261, 262 contract in the transverse direction (in a direction perpendicular to the surface of FIG. 7).

As will be understood from FIG. 8, the ventral and dorsal sheet members 202, 203 and the crotch sheet member 204 contract in the transverse direction from the flatly developed state indicated by imaginary lines to the state indicated by solid lines as the ventral and dorsal rubber strings 261, 262 are left contract in the transverse direction. At this moment, the ventral sheet member 202 contracts more significantly than the dorsal sheet member 203 and correspondingly the section of the body fluid absorbent structure 205 defined by the parallel segments on the side of the ventral sheet member 202 contracts more significantly than the section defined by the parallel segments on the side of the dorsal sheet member 203. This is for the reason that the ventral sheet member 202 involved stress higher than that involved by the dorsal sheet member 203 when the diaper 201 in its flatly developed state.

Contraction of the ventral and dorsal rubber strings 261, 262 causes the crotch sheet member 204 also to contract in the transverse direction from the rectangular shape indicated by imaginary line to the trapezoidal shape indicated by a solid line. As a result of contraction in this manner, an apparent transverse dimension of the crotch sheet member 204 is such that its width W2 on a border line with the dorsal sheet member 203 is larger than its width W1 on a border line with the ventral sheet member 202. The term "apparent transverse dimension of the crotch sheet member 204" used herein refers to a distance between the opposite side edges 241 of the crotch sheet member 204 after the transverse dimensions W1 and W2 of the crotch sheet member 204 have been reduced under contraction of the rubber strings 261, 262.

The differential width of the crotch sheet member 204 such that its width W2 on the border line with the dorsal sheet member 203 has been relatively enlarged under contraction of this sheet member 204 allows the crotch sheet member 204 to cover the wearer's buttocks over the correspondingly larger extent and thereby to improve a fit of the crotch sheet member 204 particularly to the region extending from the buttocks to the legs. In addition, the differential width of the crotch sheet member 204 such that its width W1 on the border line with the ventral sheet member 202 has been relatively smaller under contraction of this sheet member 204 makes it possible to avoid possibility that the crotch sheet member 204 might become bulky and, in consequence, such bulkiness might deteriorate feeling to wear the diaper.

Figure 9:
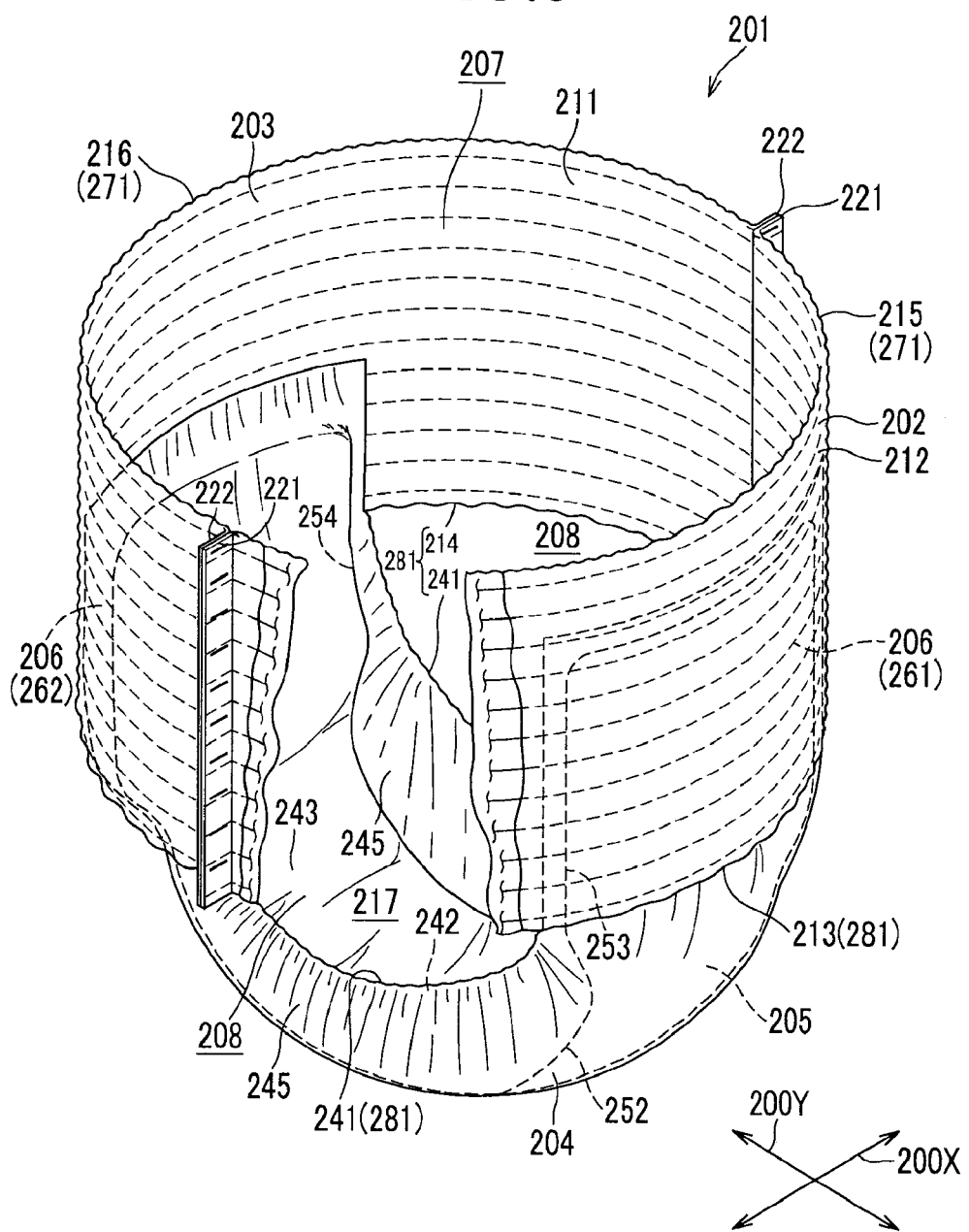
FIG. 9 is a perspective view showing the diaper as has been shaped in pants.

Referring now to FIGS. 9 through 11, the diaper 201 according to this embodiment will be described as after shaped in pants by joining the opposite side edges 221, 221 of the ventral sheet member 202 extending in the longitudinal direction with the opposite side edges 222, 222 of the dorsal sheet member 203 so that the ventral sheet member 202 and the dorsal sheet member 203 may be annularly joined together to shape the diaper 201 of FIG. 6 in pants. FIG. 9 is a perspective view showing the diaper 201 shaped in pants, FIG. 10 schematically shows the diaper 201 shaped in pants as viewed from the side of the front particularly with respect to peripheral edges 281 of the leg-openings and FIG. 11 schematically shows the diaper 201 shaped in pants as viewed from the side of the dorsal sheet member 203.

As will be apparent from FIG. 9, the diaper 201 shaped in pants has a waist-opening 207 defined by the ventral sheet member 202 and the dorsal sheet member 203 annularly joined together and a pair of leg-openings 208 defined by the front sheet member 202, the dorsal sheet member 203 and the crotch sheet member 204 joined to these two sheet members 202, 203. More specifically, referring to FIG. 6, these leg-openings 208 are defined by proximal edges 213, 214 of the front and dorsal sheet members 202, 203 extending in the transverse direction and opposed to each other behind the crotch sheet member 204 and the peripheral edges 281 comprising the opposite side edges 241 of the crotch sheet member 204. Specifically to describe, the waist-opening 207 is defined by a peripheral edge 271 which is, in turn, defined by distal edges 215, 216 extending in transverse direction in parallel to the proximal edges 213, 214 of the front and dorsal sheet members 202, 203 and spaced from each other by a distance larger than a distance by which the proximal edges 213, 214 of the front and dorsal sheet members 202, 203.

As previously described, a pair of the easily deformable side flaps 245 extend outward from the body fluid absorbent structure 205 and the elastic members 242 for the crotch region are attached under tension to these side flaps 245. These elastic members 242 for the crotch region contract when the crotch sheet member 204 is bowed with the body fluid absorbent structure 205 inside in order to shape the diaper 201 in pants. Thereupon, the side flaps 245 raise themselves up on the body fluid absorbent structure 205 between the ventral sheet member 202 and the dorsal sheet member 203, as will be seen in FIG. 9. The side flaps raising themselves up in this manner define a space 217 surrounded thereby. With the diaper 201 put on the wearer, this space 217 lies between the wearer's crotch region and the body fluid absorbent structure 205 and serves to isolate body waste absorbed by the body fluid absorbent structure 205 from the wearer's skin.

While the elastic members 242 for the crotch region would otherwise remain linearly extending between the ventral sheet member 202 and the dorsal sheet member 203 even after contraction thereof, these elastic members 242 are pulled by the side flaps 245 toward the body fluid absorbent structure 205. Consequentially, the elastic members 242 for the crotch region are curved to describe semicircular arcs between the ventral sheet member 202 and the dorsal sheet member 203 so that the opposite side edges 241 of the crotch sheet member 204 also are curved to describe similar semicircular arcs and thereby partially define the peripheral edges 281 of the respective leg-openings.

The section defined by the parallel segments 253 of the body fluid absorbent structure 205 on the ventral sheet member 202 contract more significantly than the section defined by the parallel segments 254 on the dorsal sheet member 203 and, in consequence, the crotch sheet member 204 has the apparent width W2 on the side of the dorsal sheet member 203 larger than the apparent width W1 on the side of the ventral sheet member 202. Such differential apparent width of the crotch sheet member 204 results in an advantageous feature of the invention as will be easily understood from FIG. 10 showing the diaper 201 from the side of the front. As shown, the peripheral edges 281 of the respective leg-openings describe circular arcs extending outward in the transverse direction from the ventral sheet member 202 toward the dorsal sheet member 203. In other words, the leg-openings 208 open rather forwardly of the diaper 201.

The curved segments 252 of the body fluid absorbent structure 205 are positioned aside toward the ventral sheet members 202 and therefore a section of the body fluid absorbent structure 205 extending on the front side of the wearer's inguinal region has a relatively small dimension as measured in the transverse dimension. With such dimensional relationship, there is no anxiety that the body fluid absorbent structure 205 might be compressed in the wearer's crotch region and consequentially the wearer might experience a discomfort feeling even when the wearer closes his or her legs. Furthermore, the side flaps 245 can be deformed well keeping pace with the movement of the wearer's legs even if the movement is vigorous and therefore it is unlikely that any clearance gap might be formed between the wearer's legs and the peripheral edges 281 of the respective leg-openings through which bodily fluids might leak out.

As will be apparent from FIG. 11 schematically illustrating the diaper 201 shaped in pants from the rear side thereof, the contraction percentage of the body fluid absorbent structure 205 is lower in the section thereof defined by the parallel segments 254 on the side of the dorsal sheet member than in the section thereof defined by the parallel segments 253 on the side of the ventral sheet member. In this way, the section defined by the parallel segments 253 on the side of the ventral sheet member ensures its transverse dimension sufficient to cover the wearer's buttocks.

Figure 13:
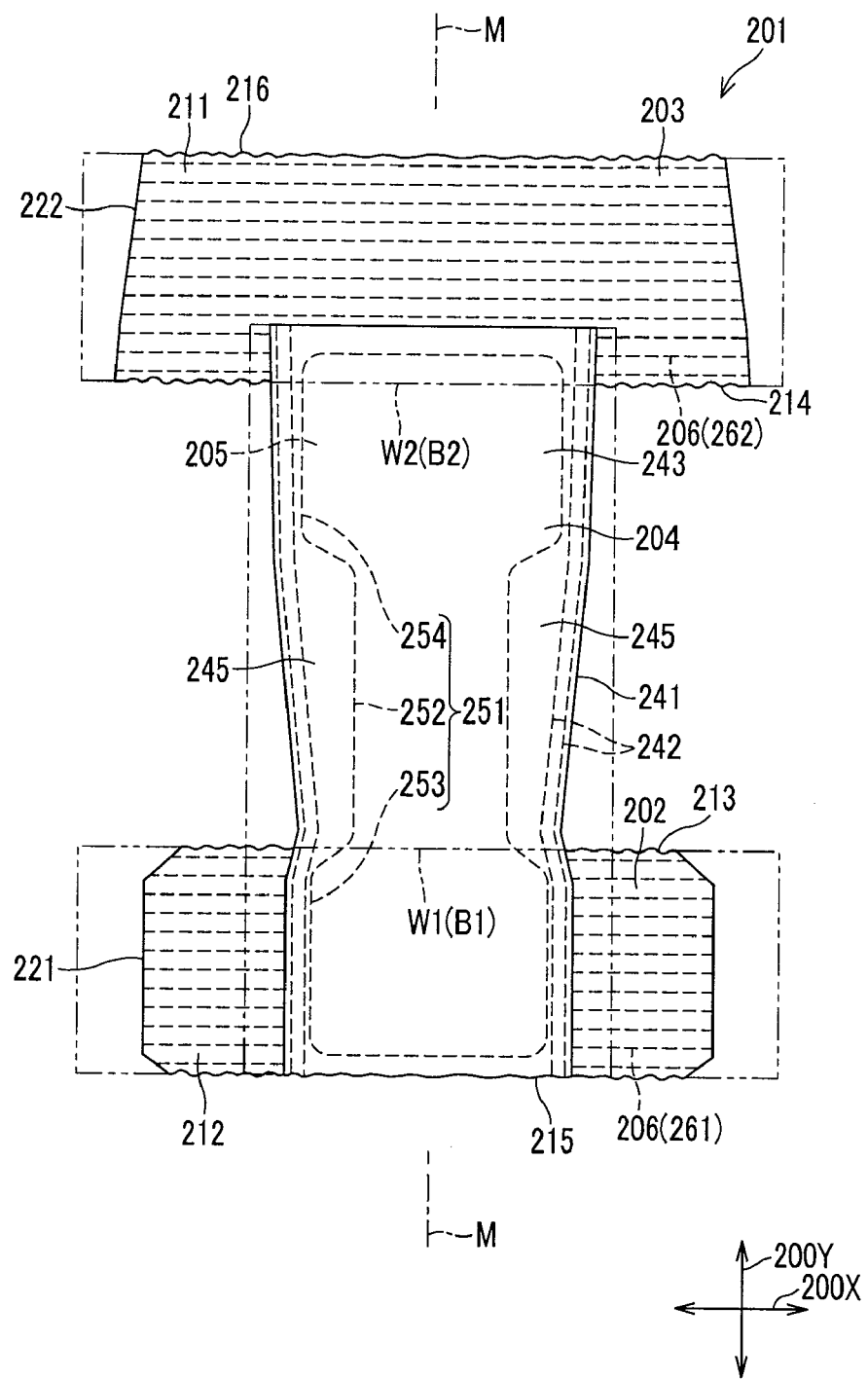
FIG. 13 is a plan view showing the diaper with the waist elastic members left contract.
Figure 14:
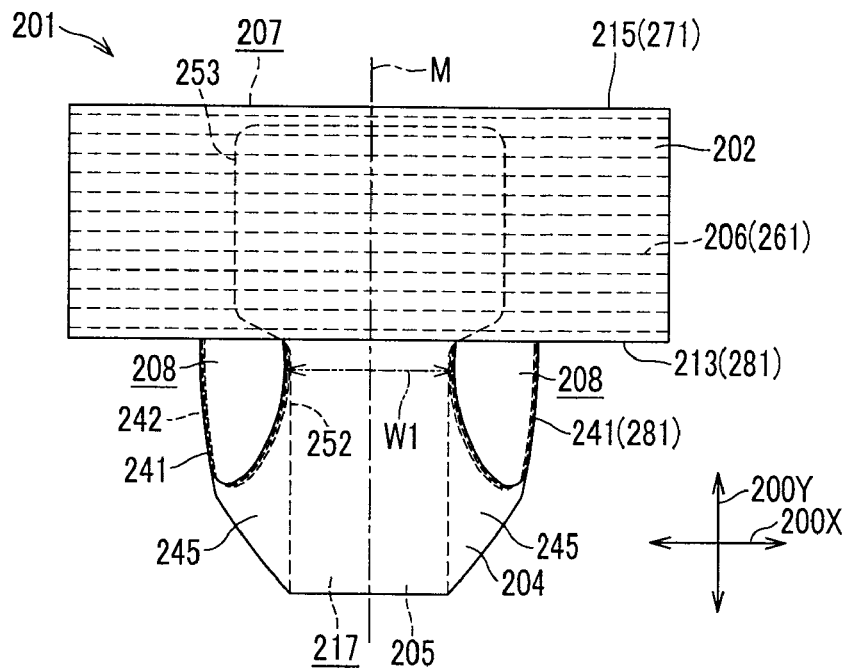
FIG. 14 schematically shows the diaper having been shaped in pants from the ventral side.
Figure 15:
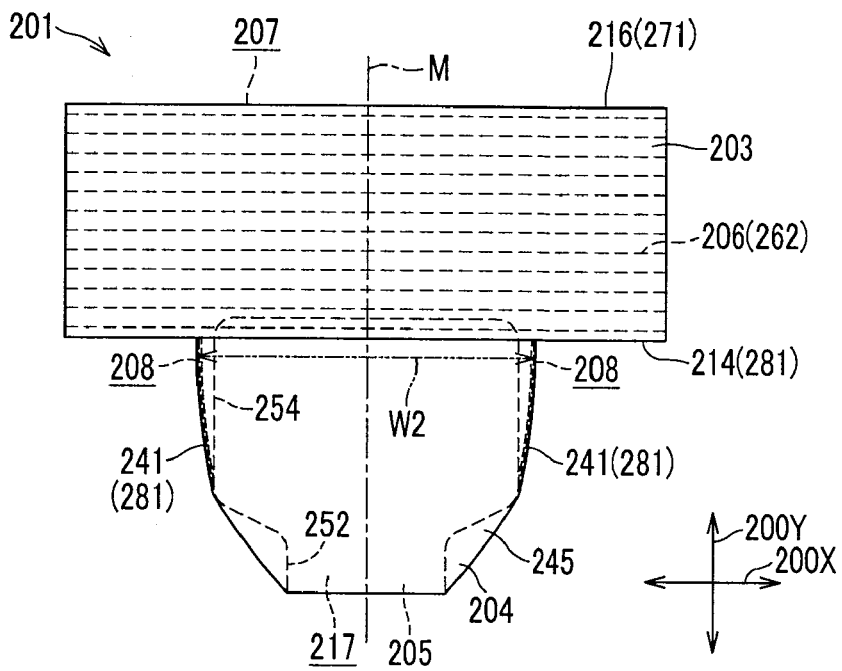
FIG. 15 schematically shows the diaper having been shaped in pants from the dorsal side.

Now a diaper 201 according to a second embodiment will be described with reference to FIGS. 12 through 15. FIG. 12 is a plan view showing the diaper 201 as flatly developed, FIG. 13 is a plan view showing the diaper 201 with the waist elastic members left contract, FIGS. 14 and 15 are schematic diagrams showing the diaper 201 shaped in pants as viewed from the ventral side and the dorsal side, respectively.

As will be understood from FIG. 12, an important difference of this embodiment from the first embodiment lies in that the curved segments 252 of the body fluid absorbent structure 205 partially overlap the ventral sheet member 202.

The crotch sheet member 204 in the second embodiment is similar to that in the first embodiment shown in FIG. 6 except that locations at which the crotch sheet member 204 is attached to the ventral sheet member 202 and the dorsal sheet member 203, respectively, are put aside toward the side of the ventral sheet member 202. In this way, the longitudinal dimension L1 by which the body fluid absorbent structure 205 overlaps the ventral sheet member 202 is larger than the longitudinal dimension L2 by which the body fluid absorbent structure 205 overlaps the dorsal sheet member 203. Alternatively, it is possible to change the locations at which the curved segments 252 are formed on the body fluid absorbent structure 205 so that the curved segments 252 may overlap a border line B1 between the ventral sheet member 202 and the crotch sheet member 204.

On the other hand, the parallel segments 254 on the body fluid absorbent structure 205 overlap a border line B2 between the dorsal sheet member 203 and the crotch sheet member 204. With this arrangement, the transverse dimension of the body fluid absorbent structure 205 is shorter on the border line B1 than on the border line B2.

The ventral sheet member 202 and the dorsal sheet member 203 respectively have the constructions similar to those in the first embodiment shown by FIG. 6. Specifically, the tensile stress of the ventral and dorsal rubber strings 261, 262 involved when the diaper 201 is flatly developed is higher in the ventral sheet member 202 than in the dorsal sheet member 203. Materials as well as modes of joining of the respective sheet members are similar to those in the first embodiment and detailed description thereof will not be repeated here.

When the ventral and dorsal rubber strings 261, 262, respectively, are left contract in the transverse direction, the ventral and dorsal sheet members 202, 203 and the crotch sheet member 204 shrink in the transverse direction from the flattened state indicated by imaginary lines to the state indicated by solid lines. Regions of the front and dorsal sheet members 202, 203 extending outside the body fluid absorbent structure 205 are relatively easy to be deformed since these regions are not affected by a relatively high stiffness of the body fluid absorbent structure 205.

This relationship can be verified by comparing a transverse length of the border line B1 between the ventral sheet member 202 and the crotch sheet member 204 with a transverse length of the border line B2 between the dorsal sheet member 203 and the crotch sheet member 204 after the ventral and dorsal rubber strings 261, 262 have contracted. In addition to the higher stress of the rubber strings 261 on the ventral side, the relatively short length over which the dorsal sheet member 203 overlaps the body fluid absorbent structure 205 leads to a dimensional relationship that the length of the border line B1 is shorter than the length of the border line B2. Thus, the apparent dimension of the crotch sheet member 204 in the transverse direction is larger on the border line B2 with the dorsal sheet member 203 than on the border line B1 with the ventral sheet member 202, i.e., the width W2 on the border line B2 is larger than the width W1 on the border line B1 with the ventral sheet member 202.

More specifically, the leg-openings 208 open rather forwardly of the diaper 201 as will be seen in FIG. 14 schematically illustrating the diaper 201 from the ventral side. On the assumption that the body fluid absorbent structure 205 of the same configuration is used for the first embodiment as well as for the second embodiments, the leg-openings 208 open further forwardly of the diaper 201 and the fit of the diaper 201 around the wearer's legs is further improved in comparison with the case of the first embodiment. This is for the reason that, as has been described above, the transverse dimension of the body fluid absorbent structure 205 on the border line B1 is larger in the second embodiment than in the first embodiment.

As will be apparent from FIG. 15 schematically illustrating the diaper 201 shaped in pants from the dorsal side, the section of the body fluid absorbent structure 205 defined by the parallel segments 254 on the side of the dorsal sheet member exhibits a contraction percentage lower than a contraction percentage exhibited by the section of the body fluid absorbent structure 205 defined by the parallel segments 253 on the side of the ventral sheet member as the first embodiment is the case. Consequentially, the transverse dimension of the body fluid absorbent structure 205 is sufficiently larger in the section defined by the parallel segments 254 on the side of the dorsal sheet member than in the section defined by the parallel segments 253 on the side of the ventral sheet member to cover the wearer's buttocks in a desired manner.

According to this second embodiment, the curved segments 252 of the body fluid absorbent structure 205 partially overlap the border line B1 between the ventral sheet member 202 and the crotch sheet member 204 while the dorsal side parallel segments 254 of the body fluid absorbent structure 205 overlap the border line B2 between the dorsal sheet member 203 and the crotch sheet member 204 so that the transverse dimension of the body fluid absorbent structure 205 on the border line B1 is smaller than the transverse dimension of the body fluid absorbent structure 205 on the border line B2. In the flatly developed state, therefore, it is possible to deform the body fluid absorbent structure 205 so that the ventral rubber strings 261 and the dorsal rubber strings 262 may exhibit the same stress. It is also possible to set the stress of the ventral rubber strings 261 to be lower than the stress of the dorsal rubber strings 262.

According to this second embodiment, the apparent width W1 of the crotch sheet member 204 along the border line B1 on which the curved segments 252 partially overlap the ventral sheet member 202 is necessarily smaller than the width W2 along the border line B2 so far as the ventral sheet member 202 shrink under contraction of the ventral rubber strings 261. It is not essential, therefore, to set a contraction percentage of the ventral sheet member 202 to a level higher than a contraction percentage of the dorsal sheet member 203.

While the disposable diaper 201 of three piece-type characterized by improved a fit thereof to the wearer particularly in the region extending from the buttocks to the legs of the wearer has been described above on the basis of the first and second embodiments, it should be understood that the present invention is not limited to these embodiments but various modifications or variations may be conceived by those skilled in the art without departing from the scope of the invention.

In one example of the conceivable variants, the ventral sheet member 202 and the dorsal sheet member 203 may be respectively provided with a plurality of waist elastic members 206 in a manner that the waist elastic members 206 extending across the body fluid absorbent structure 205 are arranged at closer intervals on the ventral sheet member 202 than on the dorsal sheet member 203. For example, the first embodiment or the second embodiment may be modified so that the ventral rubber strings 261 extending across the body fluid absorbent structure 205 are arranged at closer intervals than the dorsal rubber strings 262 on the dorsal sheet member 203. Such modification allows the ventral rubber strings 261 and the dorsal rubber strings 262 to have the same tensile stress. In FIG. 6, the number of the dorsal rubber strings 262 extending across the body fluid absorbent structure 205 may be appropriately decreased to achieve the above-mentioned modification.

It is also possible to provide the dorsal sheet member 203 with none of the waist elastic members 206 extending across the body fluid absorbent structure 205 or to increase the number of the ventral rubber strings 261 extending across the body fluid absorbent structure 205 with respect to the number of the dorsal rubber strings 262 extending across the body fluid absorbent structure 205. Preferably for such modification, the ventral and dorsal rubber strings 261, 262 have the same tensile stress and the ventral rubber strings 261 extending across the body fluid absorbent structure 205 are arranged at the intervals closer than the intervals at which the dorsal rubber strings 262 extending across the body fluid absorbent structure 205 are arranged.

In fact, it is essential that the waist elastic members 206 extending across the body fluid absorbent structure 205 should exhibit a contraction percentage higher on the side of the ventral sheet member 202 than on the side of the dorsal sheet member 203.

An alternative construction is also conceivable such that, of the waist elastic members 206 (i.e., the dorsal rubber strings 262) extending across the dorsal sheet member 203, at least the waist elastic members 206 extending in the vicinity of the border line B2 between the dorsal sheet member 203 and the crotch sheet member 204 exhibit an elasticity lower than an elasticity exhibited by the waist elastic members 206 extending across the remaining region of the dorsal sheet member 203. In other words, it is possible to construct the dorsal sheet member 203 so that the contraction percentage of the dorsal sheet member 203 depends so that at least the waist elastic members 206 extending in the vicinity of the border line B2 between the dorsal sheet member 203 and the crotch sheet member 204 exhibit an elasticity lower than an elasticity exhibited by the waist elastic members 206 extending across the remaining region of the dorsal sheet member 203. The diaper 201 according to this variant is apparently similar to the diaper 201 illustrated in FIGS. 6 through 11 and therefore not illustrated.

To differentiate the elasticity exhibited by the waist elastic members 206 or the contraction percentage of the dorsal sheet member 203 depending on the region as has been described above, some of the waist elastic members 206 may be made inelastic using various means of well known art such as cutting, heat treating or chemically treating the waist elastic members 206 present in the vicinity of the border line 32 with the dorsal sheet member 203. If some of the waist elastic members 206 extend across the body fluid absorbent structure 205, these elastic members 206 are preferably made inelastic. It is ensured thereby that the width W2 on the side of the dorsal sheet member 203 can be held as wide as possible and leak of bodily fluids due to creases which would otherwise be formed on the body fluid absorbent structure 205 can be prevented since there is no more possibility that the body fluid absorbent structure 205 might shrink in the transverse direction on the side of the dorsal sheet member 203.

Alternatively, it is possible to make the waist elastic members 206 partially inelastic also on the side of the ventral sheet member 202 and to ensure that the width W2 of the crotch sheet member 204 on the side of the dorsal sheet member 203 is larger than the width W1 on the side of the ventral sheet member 202. Assumed that the ventral rubber strings 261 and the dorsal rubber strings 262 have are made from one and same material and have characteristics such as the material, the number and the contraction percentage common to the both, the relationship as has been described above is obtained by dimensioning the extent over which the dorsal rubber strings 262 are made inelastic to be larger than the extent over which the ventral rubber strings 261 are made inelastic.

When the waist elastic members 6 on the side of the ventral sheet member 202 are partially made inelastic, the region to be flattened for the purpose of urine-leak preventing effect is preferably made inelastic in view of the fact that the body fluid absorbent structure 205 lying on the side of the ventral sheet member 202 substantially serves for absorption of urine. As a specific example, the waist elastic members 206 may be made inelastic along a peripheral edge of the body fluid absorbent structure 205 overlapping the ventral sheet member 202 to ensure that urine leakage possibly occurring in the transverse direction of the body fluid absorbent structure 205 and in a direction from the body fluid absorbent structure 205 toward the waist-openings 207 can be reliably prevented.

To cut the waist elastic members 206, an appropriate cutter may be used to cut the waist elastic members 206 together with the dorsal sheet member 203. When such cutting treatment is adopted, those of the waist elastic members 206 extending across the body fluid absorbent structure 205 may be cut. When a heat treatment is adopted to make the waist elastic members 206 on the side of the dorsal sheet member 203 inelastic, the waist elastic members 206 are preferably made of thermoplastic elastomers of well known art such as urethane-based or styrene-based elastomers.

Alternatively, the percentage of the waist elastic members 206 may be periodically varied when these waist elastic members 206 are bonded to the dorsal sheet member 203 so that at least the waist elastic members 206 lying in the vicinity of the border line B2 with the dorsal sheet member 203 may have an elongation percentage lower than an elongation percentage of the waist elastic members 206 lying in the remaining region. In this way, the elasticity exhibited by the waist elastic members 206 may be varied depending on the region occupied by these elastic members 206. It is also possible to adjust the elasticity exhibited by the waist elastic members 206 lying in the middle along the longitudinal center line M of the dorsal sheet member 203 to be lower than in the regions extending on both sides of the center line M.

With this arrangement, in comparison with the elasticity exhibited by the waist elastic members 206 lying in the vicinity of the border line B2 between the dorsal sheet member 203 and the crotch sheet member 204, the elasticity exhibited by the waist elastic members 206 lying in the remaining region is relatively high. As a result, the elasticity of the waist elastic members 206 function to enlarge the apparent transverse dimension W2 of the crotch sheet member 204 in the vicinity of the border line with the ventral sheet member 202 as the diaper 201 is shaped in pants (See FIGS. 11 and 15).

In this case also, the contraction percentage of the waist elastic members 206 on the side of the ventral sheet member 202 may be set to be higher than on the side of the dorsal sheet member 203. The elasticity of the waist elastic members 206 in the vicinity of the border line B2 with the dorsal sheet member 203 may be preferably minimized. In consequence, it is possible to obtain the diaper 201 including the crotch sheet member 204 of which the width W2 on the side of the dorsal sheet member 203 is larger than the width W1 on the side of the ventral sheet member 202.

As still another example of the conceivable variants, the body fluid absorbent structure 205 may be constructed so that a section of the structure 205 overlapping the ventral sheet member 202 more easily shrink than a section thereof overlapping the dorsal sheet member 203. Such effect may be achieved, for example, by adjusting a fiber density of fluff pulp constituting the body fluid absorbent structure 205 to be lower on the side of the ventral sheet member 202 than on the side of the dorsal sheet member 203 so that the side of the ventral sheet member 202 may be more ready for compressive deformation.

Conceivable variants are not limited to those as have been described above. For example, it is possible to use the dorsal sheet member 203 having a longitudinal dimension larger than a longitudinal dimension of the ventral sheet member 202 instead of using the ventral and dorsal sheet members 202, 203 which are the same in shape as well as in size. Alternatively, a rectangular or square sheet may be cut in two along a curve describing sinusoidal wave or a flexuous line describing saw-tooth wave both extending in the transverse direction so that one of them is to be used as the ventral sheet member 202 and the other is to be used as the dorsal sheet member 203. It is also possible to obtain the ventral sheet member 202 or the dorsal sheet member 203 by folding a single sheet in two between which a plurality of rubber strings or the like may be sandwiched.

As far as the shape of the crotch sheet member 204 is concerned, it is essential that the opposite side edges 241 thereof extending in the longitudinal direction become in parallel to each other as the diaper 201 is flatly developed and the shape of longitudinally opposite ends thereof connecting these opposite side edges 241 to each other may be linear, curved or flexuous. Each of the liquid-pervious sheet 243 and the liquid-impervious sheet 244 may comprise either a single sheet or two or more sheets.

Third Aspect of the Invention

Figure 16:
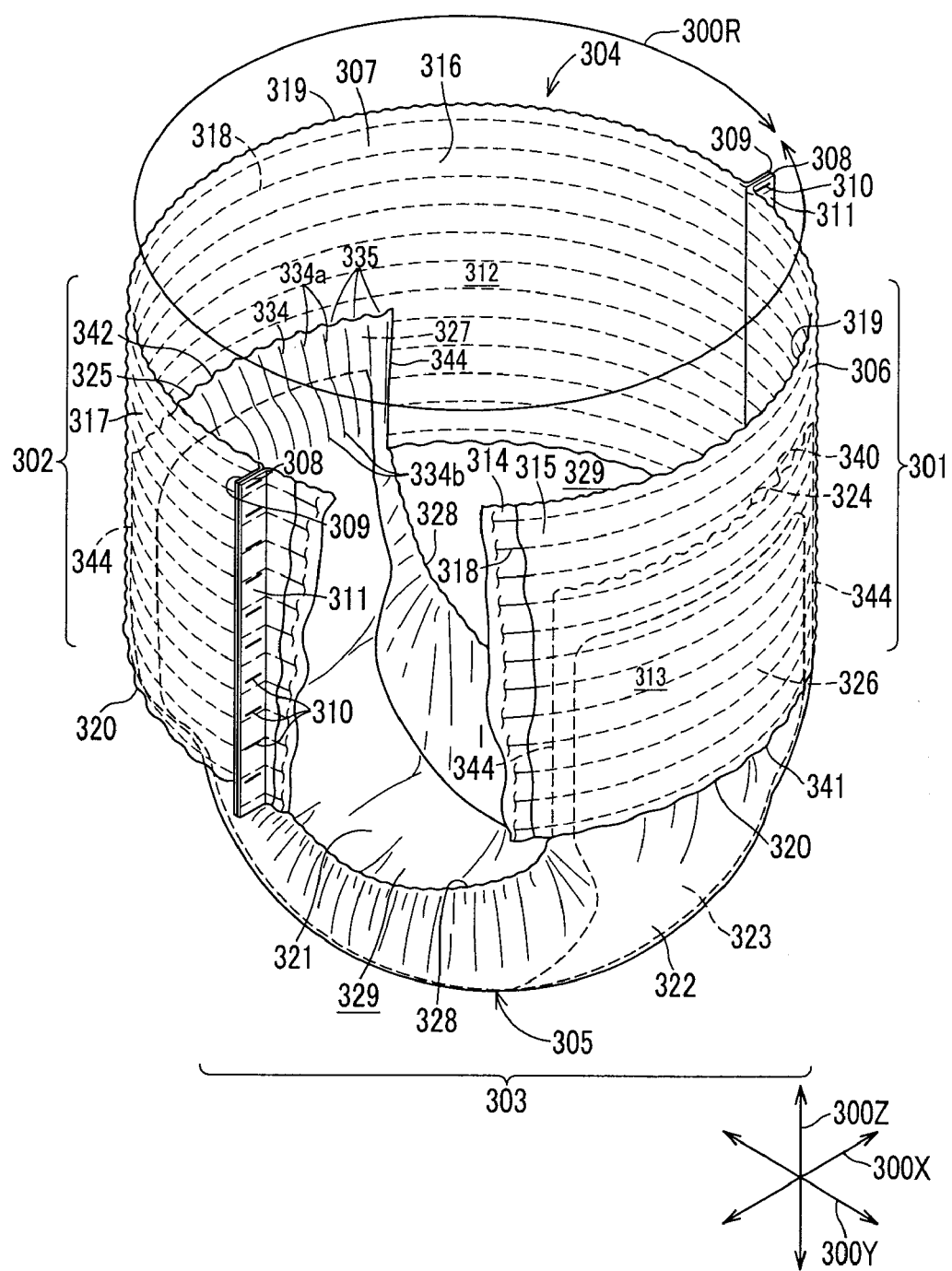
FIG. 16 is a perspective view showing the first embodiment of the present invention.

FIGS. 16 through 20 illustrate a first embodiment of the absorbent article according to the present invention on the third aspect in the form of disposable diaper as one of typical examples of the absorbent article. FIG. 16 shows the diaper actually put on the wearer's body as partially cutaway for convenience of explanation. As shown, the diaper comprises a belt member 304 annularly extending in a circumferential direction 300R to constitute a front waist region 301 and a rear waist region 302 and a liquid-absorbent structure 305 extending between the front and rear waist regions 301, 302 to constitute a crotch region 303.

The belt member 304 comprises a front belt section 306 lying on the front waist region 301 and a rear belt section 307 lying on the rear waist region 302, wherein side edges 308 of the front belt section opposite in the circumferential direction 300R and the corresponding side edges 309 of the rear belt sections 306 are put flat and joined together at seams 311 each comprising a plurality of joint zones 310 arranged along these side edges 308, 309 intermittently in a height direction 300Z to define a waist-opening.

The front belt section 306 comprises an inner sheet 314 defining an inner side 312 facing the wearer's skin, an outer sheet 315 defining an outer side 313 facing the wearer's garment and a plurality of string-like waist elastic members 318 sandwiched between these inner and outer sheets 314, 315 and serving as waist contractile means. The inner and outer sheets 314, 315 are really formed by folding a single layer of fibrous nonwoven fabric along a peripheral open edge 319 of the waist-opening back unto itself so as to sandwich the waist elastic members 318.

In a similar fashion, the rear belt section 307 comprises an inner sheet 316, an outer sheet 317 and the waist elastic members 318 sandwiched between these sheets 316, 317. The inner and outer sheets 316, 317 also are really formed by folding a single layer of fibrous nonwoven fabric along a peripheral open edge 319 of the waist-opening back unto itself. The fibrous nonwoven fabric may be selected from the group of those usually used in this technical field such as melt-blown nonwoven fabrics, point-bond nonwoven fabrics and through-air nonwoven fabrics.

The front and rear belt sections 306, 307 are provided with the waist elastic members 318 each extending in a circumferential direction 300R. These elastic members 318 are arranged intermittently in a height direction 300Z, i.e., from the open edges 319 of these belt sections 306, 307 on the side of the waist-opening to the open edges 320 thereof on the side of crotch region. These waist elastic members 318 are attached under tension to the belt sections 306, 307 so as to bias these belt sections to shrink in the circumferential direction 300R. Preferably, these waist elastic members 318 are spaced one from another by a distance of about 8 to about 10 mm in the height direction 300Z and attached the belt sections 306, 307 under the tension corresponding to a stretch ratio of 1.5 to 3.0.

The waist elastic members 18 are bonded to at least one of the inner and outer sheets 14, 15 and at least one of the inner and outer sheets 16, 17 by means of adhesive (not shown).

The liquid-absorbent structure 305 comprises a liquid-pervious topsheet 321 defining the inner side 312 facing the wearer's skin, a liquid-impervious backsheet 322 defining the outer side 313 facing the wearer's garment and a liquid-absorbent core 323 sandwiched between these top- and backsheets 321, 322 and wrapped with tissue paper (not shown) or the like, wherein the liquid-absorbent core 323 is permanently bonded to at least one of the top- and backsheets 321, 322. It is possible to use a moisture-pervious but liquid-impervious film as the backsheet 322 and, in this case, such film may be laminated with a fibrous nonwoven fabric obtained by an appropriate process such as a so-called spun bond process or a through-air process to improve a feeling of the backsheet 322 against the wearer's skin.

The liquid-absorbent structure 305 extends across the crotch region 303 in a longitudinal direction Y and includes a first end 324 and a second end 325 spaced from and opposed to each other in the longitudinal direction 300Y. The liquid-impervious backsheet 322 constituting the first end 324 is placed upon the inner sheet 314 constituting the front belt section 306 to define a first overlapping region 326 and the liquid-impervious backsheet 322 constituting the second end 325 is placed upon the inner sheet 316 constituting the rear belt section 307 to define a second overlapping region 327. In these first and second overlapping regions 326, 327, the front and rear belt sections 306, 307 are joined to the liquid-absorbent structure 305 by means of a plurality of joint zones 332 so that the respective open edges 320 of the front and rear belt sections 306, 307 on the side of the crotch region cooperate with a pair of opposite side edges 328 of the liquid-absorbent structure 305 extending in the longitudinal direction to form a pair of leg-openings 329.

Figure 17:
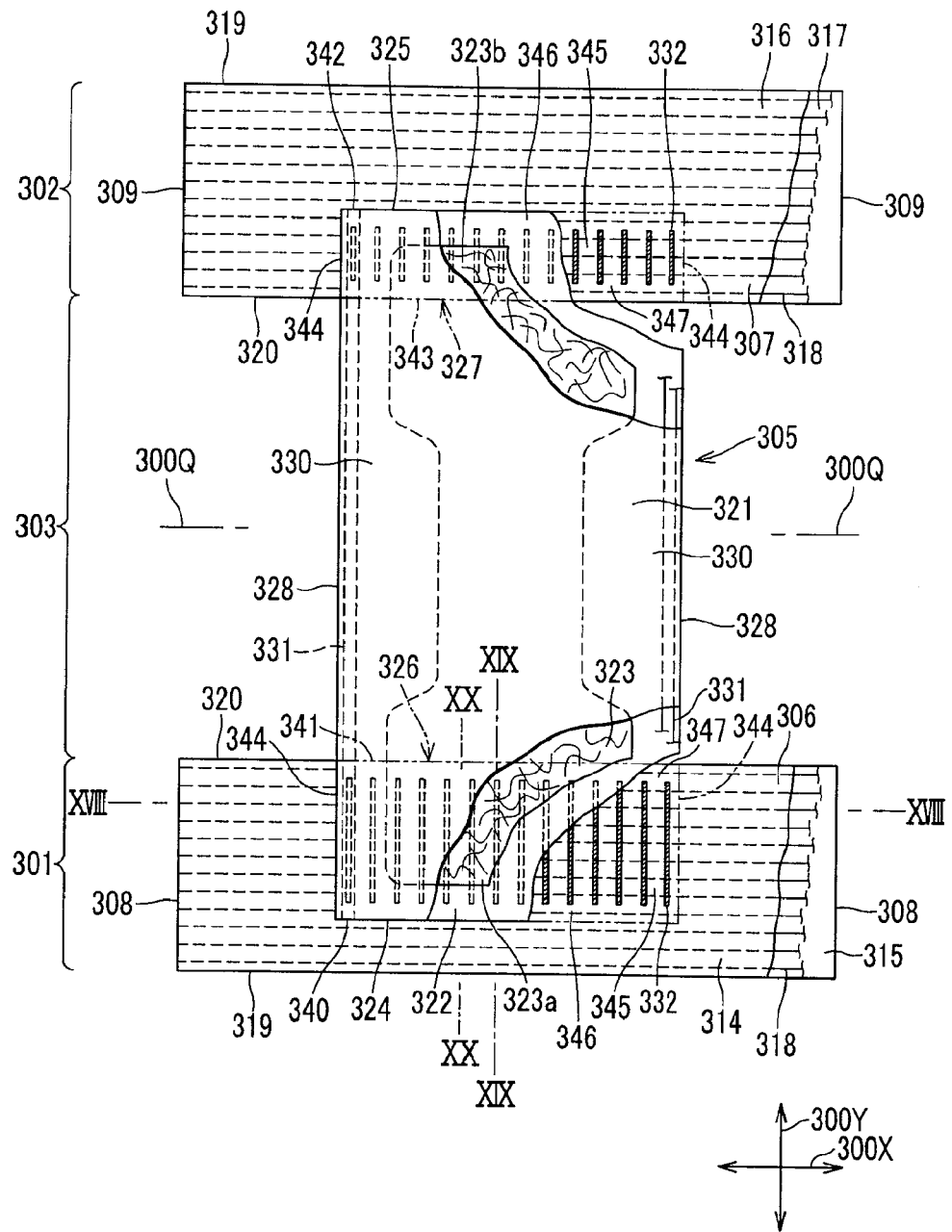
FIG. 17 is a plan view showing the diaper of FIG. 1 as flatly developed.

FIG. 17 is a plan view of the diaper flatly developed after the joint zones 310 intermittently arranged along the side edges of the diaper have been torn off. Referring to FIG. 17, the waist elastic members 318 as well as elastic members 331 for the crotch region are shown under tension without biasing the sheets to shrink.

As shown, the top- and backsheets 321, 322 of the liquid-absorbent structure 305 has substantially rectangular shapes while the liquid-absorbent core 323 has a substantially hourglass-shape. In consequence, the liquid-absorbent core 323 is partially cut out so as to have the opposite side edges curved in such a manner that a dimension of the liquid-absorbent core 323 as measured in the transverse direction 300X is smaller in the vicinity of a transverse center line 300Q bisecting the core 323 in the longitudinal direction 300Y than in the first and second ends 324, 325.

In the vicinity of the opposite side edges 328 of the liquid-absorbent structure 305, the top- and backsheets 321, 322 extend outward beyond the liquid-absorbent core 323 to form a pair of opposite side flaps 330 wherein the side flap 330 has a relatively large area in the vicinity of the transverse center line 300Q since the liquid-absorbent core 323 has the hourglass-shape. Elastic members 331 for the crotch region are sandwiched between the top- and backsheets 321, 322 so as to extend in the longitudinal direction along the opposite side edges 28 and attached the sheets 21, 22 under tension. Under contraction of these elastic members 331 for the crotch region, the opposite side edges 328 are put in close contact around the wearer's legs and the side flaps 330 serve to prevent body waste such as urine from leaking out through gaps which would otherwise be left between the leg-openings 329 and the wearer's legs (See FIG. 16).

The first and second overlapping regions 326, 327 are substantially defined in respective middles of the front and rear belt sections 306, 307 as viewed in the transverse direction 300X, leaving opposite lateral portions inclusive of the opposite side edges 308, 309 to which the liquid-absorbent structure 305 is not directly joined.

A length of the first and second overlapping regions 326, 327 measured in the longitudinal direction 300Y is approximately about 85% of the total length from the open edge 319 of the front belt section 306 on the side of the waist-opening to the open edge 319 of the rear belt section 307 on the side of the waist-opening.

The first overlapping region 326 is defined by upper and lower open edges 340, 341 spaced from and opposed to each other in the longitudinal direction 300Y and side edges 344 spaced from and opposed to each other in the circumferential direction 300R while the second overlapping region 327 is defined by upper and lower edges 342, 343 spaced from and opposed to each other in the longitudinal direction and side edges 344 spaced from and opposed to each other in the circumferential direction 300R. The upper edge 340 of the first overlapping region 326 corresponds to the first end 324 of the liquid-absorbent structure 305 and the lower edge 341 corresponds to the open edge 320 of the front belt section 306 on the side of the crotch region. The opposite side edges 344 of the respective overlapping regions correspond to the opposite side edges 328 of the liquid-absorbent structure 305. The upper edge 342 of the second overlapping region 327 corresponds to the second end 325 of the liquid-absorbent structure 305 and the lower edge 343 corresponds to the open edge 320 of the rear belt section 307 on the side of the crotch region. The opposite side edges 344 correspond to the opposite side edges 328 of the liquid-absorbent structure 305.

In the first and second overlapping regions 326, 327, the backsheet 322 of the liquid-absorbent structure 305 is bonded to the inner sheets 314, 316 of the front and rear belt sections 306, 307 at the respective joint zones 332 by means of adhesive. The joint zones 332 are arranged intermittently in the transverse direction 300X and first joint-free zone 345 in which no adhesive is present is defined between each pair of the adjacent joint zones 332. Each of the joint zones 332 preferably has a dimension of about 3 to about 50 mm as measured in the transverse direction 300X. If this dimension is less than about 3 mm, it will be impossible to assure a desired adhesive effect sufficient to prevent the sheet from peeling. If this dimension exceeds about 50 mm, it will be impossible to space each pair of the adjacent joint zones from each other by a desired distance and to assure a desired dimension of the first joint-free zone 345 as measured in the transverse direction 300X. The first joint-free zone 345 preferably has its dimension in the transverse direction 300X in a range of about 3 to about 15 mm. If this dimension is less than about 3 mm, it will be difficult for the first joint-free zone 345 to form a vent channel as will be described more in detail and if this dimension exceeds about 15 mm, it will be impossible to assure a desired width of the joint zone 332.

In the vicinity of the upper and lower edges 340, 341 and 342, 343 of the first and second overlapping regions 326, 327, respectively, second joint-free zones 346, 347 containing no adhesive are defined. These second joint-free zones 346, 347 extend over the entire areas of the first and second overlapping regions 326, 327 in the transverse direction 300X. A dimension from the upper and lower edges 340, 341, 342, 343 to ends of the respective joint zones 332 in the longitudinal direction 300Y is about 10 mm. It should be noted that this dimension has been selected in consideration of a preventive effect against unintentional peel-off and should not be construed to be limited to this value. Specifically, this dimension may be in a range of about 5 mm to about 30 mm.

The belt member 304 is provided over the entire area extending from the open edge 319 on the side of the waist-opening to the open edge 320 on the side of the crotch region with the waist elastic members 318. Thus the waist elastic members 318 extend across the first and second overlapping regions 326, 327 so as to be distributed over the entire areas of these regions 326, 327 in the longitudinal direction 300Y. The waist elastic members 318 fully extend in the transverse direction 300X between the opposite side edges 308, 309 of the respective belt sections 306, 307 so that the waist elastic members 318 are distributed over the entire areas of these regions 326, 327 in the transverse direction 300X. In this way, the entire areas of the first and second overlapping regions 326, 327 are subjected to the contractile force of the waist elastic members 318.

The first and second overlapping regions 326, 327 contain a pair of ends 323a, 323b of the liquid-absorbent core 323 spaced from and opposed to each other in the longitudinal direction 300Y so that the liquid-absorbent core 323 is also subjected to the contractile force of the waist elastic members 318.

FIG. 18 is a sectional view taken along the line XVIII-XVIII in FIG. 17. While FIG. 18 shows the front waist region 301, the rear waist region 302 also will be described with reference to FIG. 18 since the rear waist region 302 is similar to the front waist region 301 so far as the basic construction is concerned. FIG. 18A illustrates the waist elastic members 318 as held in a stretched state thereof and, as will be apparent from FIG. 18A, the waist elastic members 318 are sandwiched between the outer sheets 315, 317 and the inner sheet 314, 316 of the front and rear belt sections 306, 307, respectively, and bonded to these sheets by means of adhesive (not shown). The inner sheets 314, 316 are bonded to the backsheet 322 of the liquid-absorbent structure 305 by means of the intermittently arranged joint zones. Between each pair of the adjacent joint zones 332, the first joint-free zone 345 is defined.

FIG. 18B illustrates the waist elastic members 318 as left contract in the direction indicated by an arrow. Under contraction of the waist elastic members 318, the top- and backsheets 321, 322 and the liquid-absorbent core 323 sag at the first joint-free zones 345 to protrude upward as viewed in FIG. 18B against the wearer's skin and, in consequence, a plurality of trough-like first vent channels between the topsheet 321 and the wearer's skin. A plurality of protuberances each formed between a pair of the adjacent first vent channels 334 come in contact with the wearer' skin but the trough-like first vent channels 334 are spaced from the wearer's skin so that a plurality of cavities may be formed between these first vent channels 334 and the wearer' skin. In response to protruding upward of the liquid-absorbent structure 305 toward the wearer' skin in the first joint-free zones 345, a plurality of cylindrical second vent channels 335 are formed between the inner sheets 314, 315 of the front and rear belt sections 316, 317, respectively, and the backsheet 322 of the liquid-absorbent structure 305.

Figure 19:
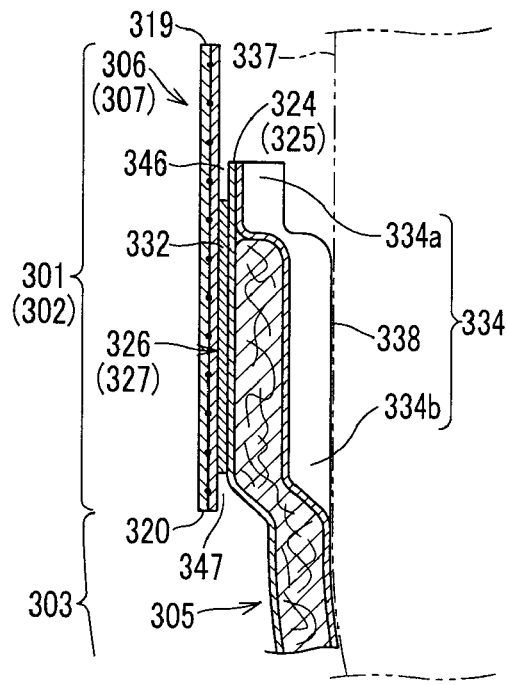
FIG. 19 is a sectional view taken along the line XIX-XIX in FIG. 17.

FIG. 19 is a sectional view taken along the line XIX-XIX in FIG. 17, i.e., showing the joint zones 332 in a sectional view. While FIG. 19 shows the front waist region 301 as put on the wearer's body, the rear waist region 302 also will be described with reference to FIG. 19 since the rear waist region 302 is similar to the front waist region 301 so far as the basic construction is concerned. As will be apparent from FIG. 19, the first vent channels 334 are formed along the respective joint zones 332 and extend from the first and second ends 324, 325 of the first and second overlapping regions 326, 327, respectively, to the open edges 320 on the side of the crotch region in the height direction. Therefore, each of the first vent channels 334 has one end 334a opens toward the front or rear waist region 301, 302 and the other end 334b thereof opens toward the crotch region 303. In this way, these first vent channels 334 allow the amount of vapor generated in the crotch region 303 to be guided along the wearer's ventral and dorsal sides toward the front and rear waist regions 301, 302.

Figure 20:
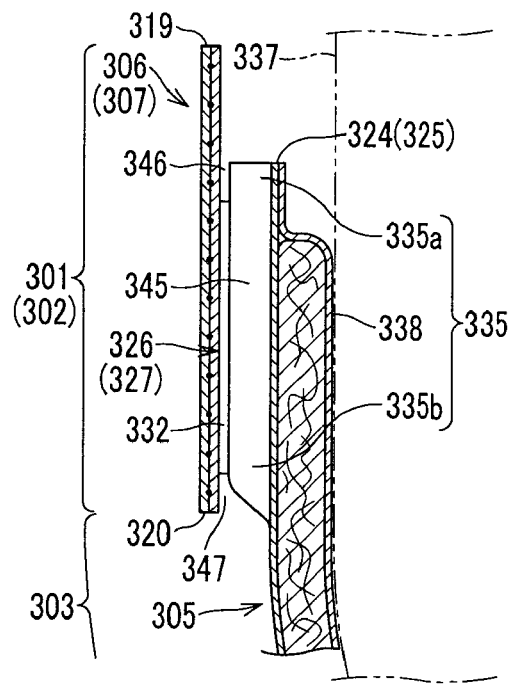
FIG. 20 is a sectional view taken along the line XX-XX in FIG. 17.

FIG. 20 is a sectional view taken along the line XX-XX in FIG. 17, showing the first joint-free zones 345 in a sectional view. While FIG. 20 illustrates the front waist region 301 as put on the wearer's boy, the rear waist region 302 also will be described with reference to FIG. 20 since the rear waist region 302 is similar to the front waist region 301 so far as the basic construction is concerned. The second vent channels 335 are formed by along the first joint-free zones 345. Via the second joint-free zones 346, 347, each of the second vent channels 335 has one end 335a communicating with the front or rear waist region 1, 2 and the other end 35b communicating with the crotch region 303 and then communicating with the exterior of the diaper via the open edges 320 of the front and rear belt sections 306, 307 on the side of the crotch region. Specifically, along the upper and lower edges 340, 341 and 342, 343 of the first and second overlapping regions 326, 327, respectively, the amount of vapor generated in the diaper can be guided through the second joint-free zones 346 to the second vent channels 335 and through the second joint-free zones 347 to the exterior of the diaper from top to bottom as viewed in FIG. 20.

According to the present invention on the third aspect, the amount of vapor generated in the crotch region 303 is guided through the first vent channels 334 to the front and rear waist regions 301, 302 while the amount of vapor staying in the front and rear waist regions 301, 302 is guided through the second vent channels 335 to the exterior of the diaper. Even if the liquid-absorbent has absorbed urine discharged by the wearer and, in consequence, a temperature within the diaper around the crotch region 303 rises, the amount of vapor generated in the crotch region can be guided through the first and second vent channels 334, 335 to the exterior of the diaper. Thereby a wet feeling experienced by the wearer can be alleviated.

The first vent channels 334 and the second vent channels 335 are formed by the top- and backsheets 321, 322 of the liquid-absorbent structure 305 and the liquid-absorbent core 323 and these first and second vent channels 334, 335 are rarely collapsed under the wearer's body weight or the other load since particularly the liquid-absorbent core 323 has a stiffness higher than those of the other sheets.

In the vicinity of the upper and lower edges 340, 341, 342, 343 of the first and second overlapping regions 326, 327, respectively, the second joint-free zones 346, 347 are distributed over the entire areas of these overlapping zones 326, 327 in the transverse direction 300X. These second joint-free zones 346, 347 allow the second vent channels 335 to fluid-communicate one with another. Therefore, even if the ends 335a or the other ends 335b of the second vent channels 335 are partially collapsed due to the movement of the wearer, it is unlikely that the breathability might be deteriorated due to such situation since the remaining second vent channels 335 are kept to fluid-communicate one with another via the second joint-free zones 346, 347.

While the waist elastic members are used as the waist contractile means in the embodiment as has been described hereinabove, it is possible without departing from the scope of the invention to use another means such as an elasticized sheet. Furthermore, the belt member itself is formed by an elasticized nonwoven fabric or a composite sheet consisting of an elastic nonwoven fabric and an inelastic nonwoven fabric so that the belt member itself may function as the waist contractile means.

While the waist elastic members 318 have been described hereinabove to be distributed substantially over the entire area of the belt member 304, it is possible to distribute these elastic members 318 over an appropriate part of the belt member 304 so far as these elastic members 318 extend across at least the portions of the first and second overlapping regions 326, 327 overlapping the liquid-absorbent structure 305 and thereby bias the liquid-absorbent structure 305 to shrink. The entire areas of the first and second overlapping regions 326, 327 in the transverse direction 300X may be subjected to the contractile force of the waist elastic members 318 to form much more vent channels in the transverse direction 300X of these overlapping regions and thereby to improve the breathability of the diaper.

While the first and second overlapping regions 326, 327 have been described hereinabove to be provided along the upper and lower edges 340, 341, 342, 343 thereof with the second joint-free zones 346, these second joint-free zones 346 may be eliminated without departing from the scope of the invention. Instead, it is possible to distribute the first and second vent channels 334, 335 over the entire areas of the first and second overlapping regions 326, 327, respectively, in the longitudinal direction 300Y so that the crotch region 303 may directly fluid-communicate with the front and rear waist regions 301, 302 in the first joint-free zones 345. Anyway, it is important that the amount of vapor generated in the crotch region 303 can be guided through the first vent channels 334 to the front and rear waist regions 301, 302 and the amount of vapor staying in the front and rear waist regions 301, 302 can be guided to the exterior of the diaper through the second vent channels 335.

While the joint zones 332 have been described hereinabove to be formed by bonding the front and rear belt sections 306, 307 to the liquid-absorbent structure 305 by means of hot melt adhesive, the type of adhesive is not limited to the hot melt adhesive and, instead of using adhesive, it is possible to use ultrasonic sealing techniques to form these joint zones 332.

Figure 21:
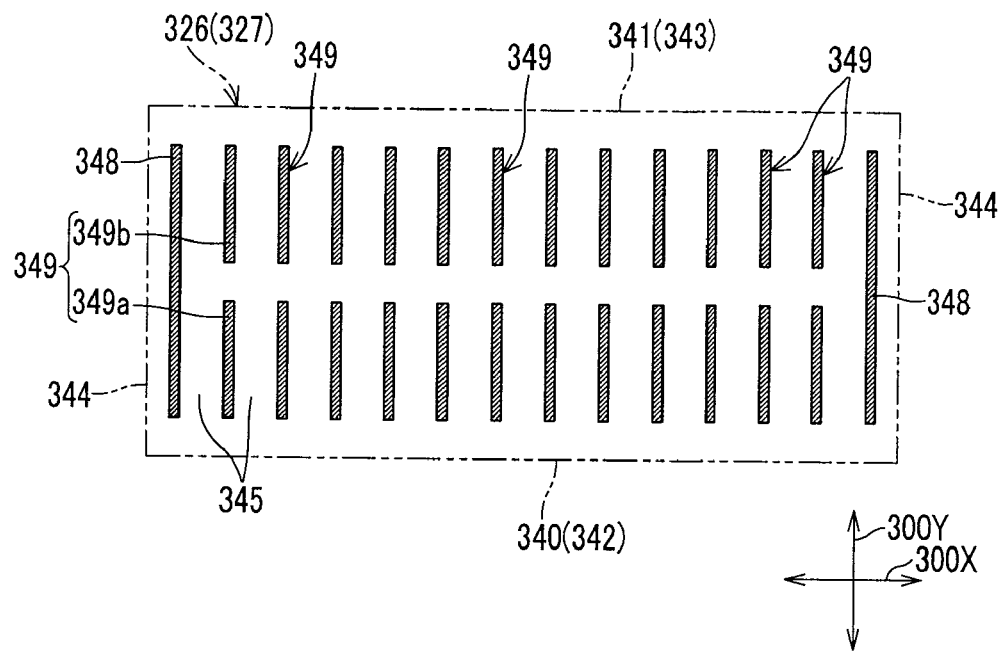
FIG. 21 is a scale-enlarged diagram illustrating the first and second overlapping regions according to the second embodiment.

FIG. 21 shows a second embodiment of the present invention in a plan view similar to FIG. 17, particularly illustrating, in an enlarged scale, the first overlapping region 326. The second overlapping region 327 also will be described with reference to FIG. 21 since the second overlapping region 327 is similar to the first overlapping region 326 so far as the basic construction is concerned. This second embodiment is characterized in that the joint zones comprise continuous joint zones 348 and intermittent joint zones 349 both with respect to the longitudinal direction. The other features are similar to those of the first embodiment and detailed description thereof will be eliminated here.

The first and second overlapping regions 326, 327 are provided in the vicinity of the respective side edges 344 with the continuous joint zones 348 one for each of the side edges 344 and with a plurality of the intermittent joint zones 349 arranged between each pair of the continuous joint zones 348 transversely opposed to each other. Each of the intermittent joint regions 349 comprises a first segment 349a and a second segment 349b spaced from each other substantially in the middle as viewed in the longitudinal direction 300Y. The first and second segments 349a, 349b are spaced from each other by a distance of about 5 mm, preferably in a range of about 3 mm to about 10 mm. If this distance is less than about 3 mm, it will be impossible to achieve a desired breathability and, if this distance exceeds about 10 mm, a bonding strength will be insufficient.

The intermittent joint zones 349 allow the first joint-free zones 345 to fluid-communicate one with another substantially at the respective middles in the longitudinal direction 300Y of the first and second overlapping regions 326, 327. Specifically, the second vent channels 334 formed by the first joint-free zones 345 fluid-communicate one with another via the gaps defined between the first and second segments 349a, 349b of the respective intermittent joint zones 349. Consequentially, even if the upper and lower ends the second vent channels 334 collapse on the sides of the upper and lower edges 340, 341 and 342, 343, the amount of vapor generated in the crotch region can be guided to the exterior of the diaper since the second vent channels 334 are kept in fluid-communication with the first joint-free zones 345 at the middles thereof. In this way, there is no anxiety that the crotch region might partially remain wetted due to a residual amount of vapor failed to be guided to the exterior of the diaper.

A pair of the continuous joint zones 348 each formed in the vicinity of the associated side edge 344 serve to guide the amount of vapor generated in the crotch region through the second vent channels 334 to the exterior of the diaper without leaking outward in the transverse direction 300X. While each of the opposite side edges 344 is provided with the single continuous joint zone 348 in this embodiment, the number of the continuous joint zones 348 is not limited to this embodiment and two or more continuous joint zones 348 may be provided along each of the opposite side edges 344 so far as it is assured that leak of vapor in the transverse direction 300X is reliably prevented.

Figure 22:
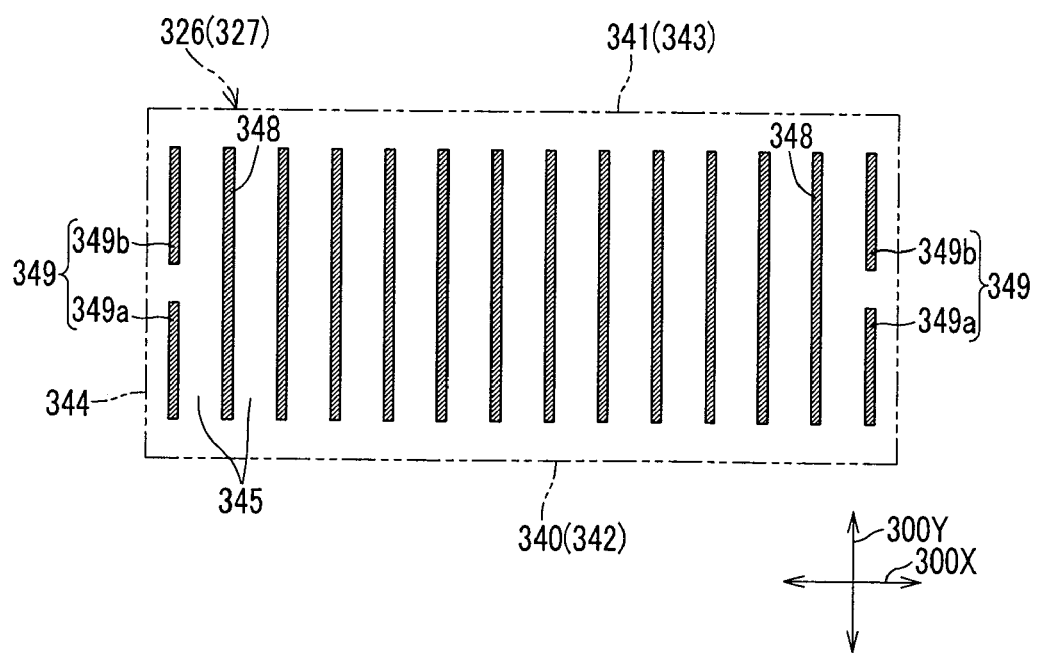
FIG. 22 is a diagram similar to FIG. 21, illustrating one variant of the second embodiment.

While the continuous joint zones 348 are provided in the vicinity of the opposite side edges 344 in this embodiment, it is possible to provide the intermittent joint zones 349 in the vicinity of the respective side edges 344 as will be seen in FIG. 22. In this variant shown by FIG. 22, a plurality of the continuous joint zones 348 are arranged between the intermittent joint zone 349 provided in the vicinity of the one side edge 344 and the intermittent joint zone 349 provided in the vicinity of the other edge 344. It is also possible to arrange the continuous joint zones 348 and the intermittent joint zones 349 alternately in the transverse direction 300X. The intermittent joint zones 349 allow the first joint-free zones 345 each extending in the longitudinal direction 300Y to fluid-communicate one with another and thereby allow the second vent channels 335 formed by these first joint-free zones 345 to fluid-communicate one with another. The second vent channels 335 thus fluid-communicate one with another in the transverse direction 300X and, even if these second vent channels 335 are collapsed on the side of the upper and lower edges 340, 341, such fluid-communication assures that the amount of vapor generated in the crotch region can be reliably guided to the exterior of the diaper.

Figure 23:
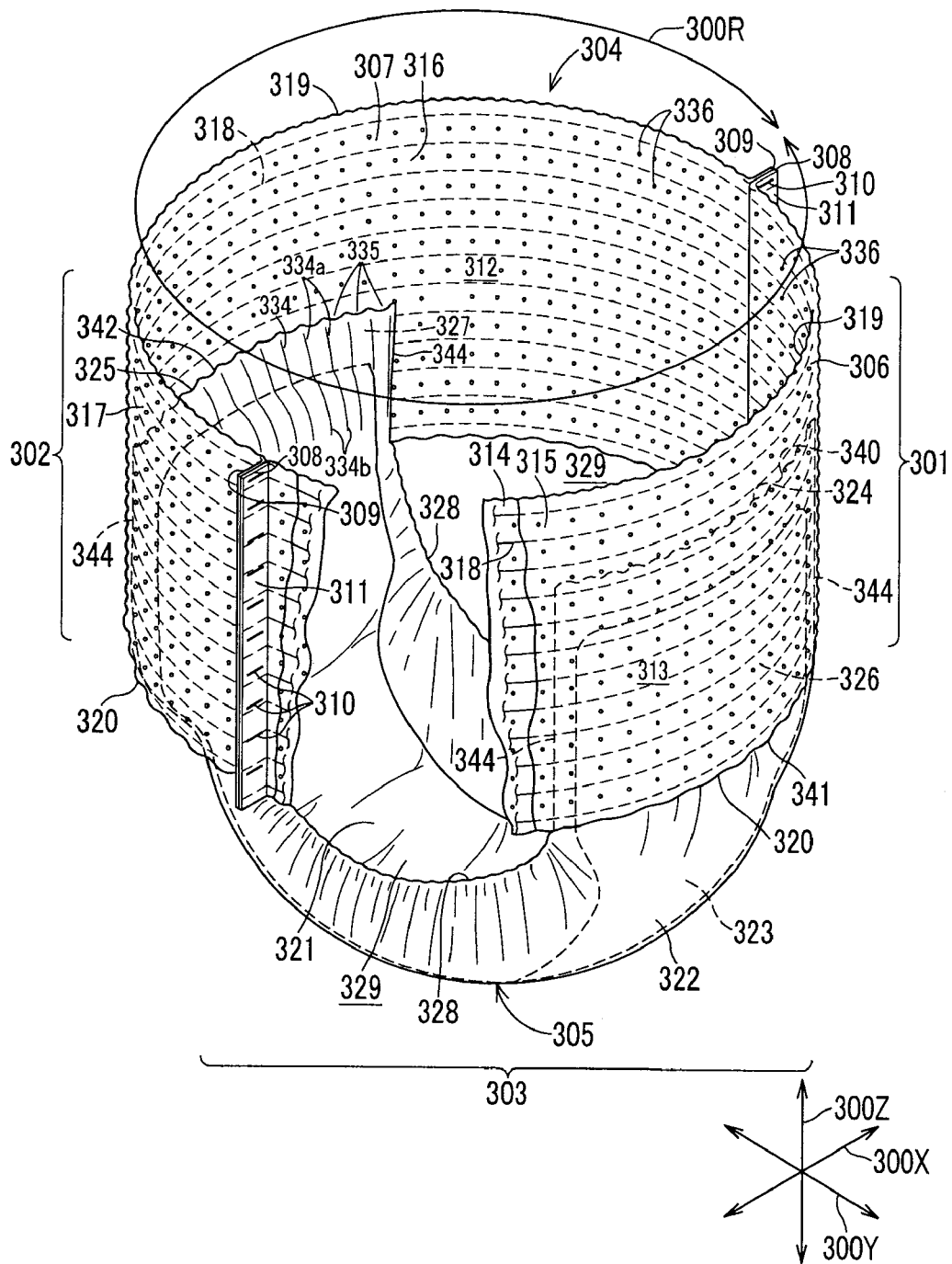
FIG. 23 is a perspective view showing the third embodiment.
Figure 24:
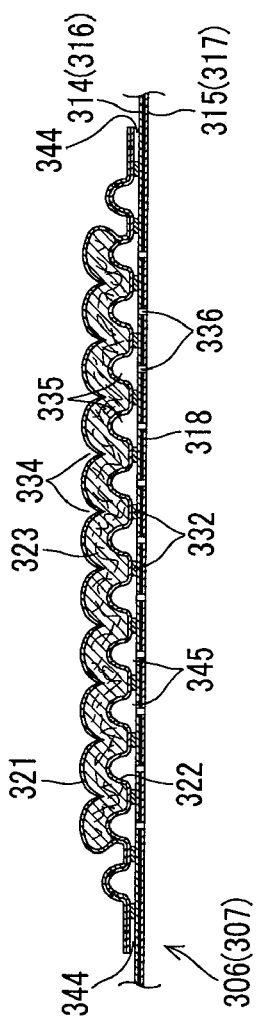
FIG. 24 is a view similar to FIG. 18B, illustrating the third embodiment.

FIGS. 23 and 24 show a third embodiment of the present invention wherein FIG. 23 is a perspective view of the diaper as a whole according to this embodiment FIG. 24 is a sectional view similar to FIG. 18B. The third embodiment is characterized in that the belt member 304 is provided with a plurality of vent holes 336 each extending through the belt member 304 in its thickness direction. The other features are similar to those of the first embodiment and detailed description thereof will be eliminated here.

The front and rear belt sections 306, 307 are provided over the entire areas of the inner and outer sheets 314, 315 and the inner and outer sheets 316, 317, respectively, with a plurality of the vent holes 336 each extending through these sheets in the thickness direction. These vent holes 336 are preferably arranged in the first joint-free zones 345 as will be seen in FIG. 24. This is for the purpose of preventing the vent holes 336 from being clogged by adhesive forming the joint zones 332. Each of the vent holes 332 preferably has a diameter of about 1 mm to about 2 mm and preferably arranged not to overlap the waist elastic members 318 provided on the front and rear belt sections 306, 307.

Such arrangement of the vent holes 336 allows the amount of vapor guided into the second vent channels 335 to be further guided though these vent holes 336 to the exterior of the diaper and thereby allow any wet feeling experienced by the wearer to be further alleviated.

FIG. 25 shows a fourth embodiment of the present invention. This fourth embodiment is characterized in that the first and second ends 324, 325 of the liquid-absorbent structure 305 are provided with cover sheets 350, respectively, in order to prevent the liquid-absorbent core 323 from falling off through clearance gaps between the top- and backsheets 321, 322. The other features are similar to those of the first embodiment and detailed description will be eliminated here.

The cover sheet 350 presents a ventilation rate of 113 kPa·S/m² and formed from a sweat-absorbent sheet having antibiotic properties. These cover sheets 350 cover the first and second ends 324, 325 and permanently bonded to the inner sheets 314, 316 of the front and rear belt sections 306, 307. The cover sheet 350 has a pair of side edges 350c opposed to and spaced from each other in the transverse direction 300X and a pair of ends 350a, 350b opposed to and spaced from each other in the longitudinal direction 300Y. A dimension measured from the one side edge 350c to the other side edge 350c in the transverse direction 300X substantially equal to a dimension of the respective belt sections 306, 307, i.e., to a dimension from the one side edge 308, 309 to the other side edge 308, 309.

The inner ends 350a are fully opposed to and joined to the inner sheets 314, 316, respectively, by means of adhesion or welding. The outer ends 350b overlap in the vicinity of the respective middles thereof the inner sheets 314, 316, respectively, and are joined thereto by means of adhesion or welding. Specifically, the cover sheets 350 extend from the inner ends 350a joined to the inner sheets 314, 316 to the outer ends 350b joined to the topsheet 321 and the inner sheets 314, 316 so as to straddle and cover the first and second ends 324, 325, respectively. With such unique construction, there is no anxiety that the liquid-absorbent core 323 might fall off in the unlikely event that the first and/or second ends 324, 325 partially open due to deterioration of adhesion. The liquid-absorbent core 323 comprises hydrophilic pulp and super-absorbent polymer particles and, if these components fall off through the first and/or second ends 324, 325, the wearer's skin will be undesirably irritated. Particularly, the polymer particles are of extremely small size and apt to fall off even through a fine clearance gap. As the effective countermeasure against this, the cover sheets 350 reliably prevent the pulp and/or the polymer particles from falling off.

Although it is inevitable in this embodiment that the cover sheets 350 close up the outer ends 335a of the second vent channels 335, the desired ventilation rate of the second vent channels 335 can be assured by setting the ventilation rate of the cover sheets about 350 to about 113 kPa·S/m². It should be noted here that the ventilation rate is not limited to this specific value and it is possible to prevent the liquid-absorbent core 323 from falling off without interfering with desired ventilation by the second vent channels 335 so far as the ventilation rate is set to a value of about 0.15 kPa·S/m² or less.

The ventilation rate was measured on the basis of Frajour type testing method.

By dimensioning the cover sheet 350 in the transverse direction 300X in coincidence with the dimension of the front and rear belt sections 306, 307 in the transverse direction 300X, it is possible in the course of making the diaper to cut the cover sheets 350 together with the front and rear belt sections 306, 307 on which the respective cover sheets 350. In consequence, the number of the steps of the process can be advantageously reduced.

The cover sheets 350 can serve not only to prevent the liquid-absorbent core 323 from falling off but also to absorb sweat of the wearer in order to assure a discomfort feeling to wear since sweat-absorbent sheets are used as the cover sheets 350.

The invention claimed is:

1. An absorbent article comprising:
a chassis having
a longitudinal direction and a transverse direction,
an inner side for facing a wearer's skin and an outer side for facing away from the wearer's skin,
a front waist region, a rear waist region and a crotch region extending between said front and rear waist regions, wherein
said front and rear waist regions define a waist-opening having a peripheral edge that has first and second segments, the first and second segments are opposed to each other in said longitudinal direction,
said front waist region is defined by a first fibrous nonwoven fabric folded back onto itself along a first fold line defining the first segment of the peripheral edge of the waist-opening, the first fibrous nonwoven fabric including an inner sheet defining the inner side of the front waist region and an outer sheet defining the outer side of the front waist region, and
said rear waist region is defined by a second single fibrous nonwoven fabric folded back onto itself along a second fold line defining the second segment of the peripheral edge of the waist-opening, the second fibrous nonwoven fabric including an inner sheet defining the inner side of the rear waist region and an outer sheet defining the outer side of the rear waist region; and
see-through regions in said front and rear waist regions in which for allowing the wearer's skin to be seen through the inner and outer sheets in use, wherein said see-through regions are defined by the inner and outer sheets forming the front and rear waist regions and having a total light transmittance of about 55% or higher and respectively occupy about 40% or more of said front and rear waist regions; and
a reinforcing elastic member attached to the chassis along said peripheral edge of the waist-opening and extending along the first and second fold lines in said transverse direction.

2. The absorbent article according to claim 1, wherein the front and rear waist regions comprise through-holes extending through the inner and outer sheets defining the corresponding front and rear waist regions for allowing the wearer's skin to be visible from outside in use.

3. The absorbent article according to claim 2, wherein
the chassis further comprises waist elastic members provided at the front and rear waist regions and adjacent to each other in the longitudinal direction, and
the through-holes are arranged between the reinforcing elastic member and one of the waist elastic member adjacent to the reinforcing elastic member in the longitudinal direction.

4. The absorbent article according to claim 1, wherein
the crotch region is joined to the front and rear waist region to define a first joint region between the crotch region and the front waist region and a second joint region between the crotch region and the rear waist region, and
a remaining portion of the front waist region except the first joint region and a remaining portion of the rear waist region except the second joint region define the see-through regions.

5. The absorbent article according to claim 1, wherein the total light transmittance of about 55% or higher of the inner and outer sheets forming the front and rear waist regions provides a cool feeling to the eye.

6. An absorbent article substantially symmetric about a longitudinal center line thereof, said absorbent article comprising:
a longitudinal direction and a transverse direction orthogonal to the longitudinal direction;
a ventral sheet member and a dorsal sheet member extending in parallel to each other in the transverse direction; and
a crotch sheet member extending in the longitudinal direction and joined to said ventral sheet member and said dorsal sheet member so as to connect said ventral and dorsal sheet members to each other,
wherein
said crotch sheet member has a transverse dimension smaller than those of said ventral and dorsal sheet members,
said ventral sheet member and said dorsal sheet member are provided with waist elastic members bonded thereto under tension in the transverse direction,
said ventral sheet member has at least a region in which said waist elastic members are present and said crotch sheet member overlap said waist elastic members,
said crotch sheet member has side edges opposite in the transverse direction and extending in the longitudinal direction are in parallel to each other at least when the absorbent article is flatly developed and
an apparent width of said crotch sheet member as measured in the transverse direction after said waist elastic members have been left contract, and thereby said crotch sheet member has been left shrink together with said ventral sheet member and said dorsal sheet member, is larger on a border line with said dorsal sheet member than on a border line with said ventral sheet member.

7. The absorbent article according to claim 6, wherein said crotch sheet member includes a body fluid absorbent structure, and
a longitudinal dimension of a first overlapping region where the body fluid absorbent structure overlaps the ventral sheet member is larger than that of a second overlapping region where the body fluid absorbent structure overlaps the dorsal sheet member.

8. The absorbent article according to claim 7, wherein an edge of the crotch sheet member is flush with an edge of the ventral sheet member.

9. An absorbent article having a height direction, a longitudinal direction and a circumferential direction, said absorbent article comprising:
front and rear belt members annularly defining a front waist region and a rear waist region in said circumferential direction; and
a liquid-absorbent structure defining a crotch region extending between said front and rear waist regions,
wherein
said belt members include waist contractile members biasing said belt members to shrink in said circumferential direction,
said liquid-absorbent structure has first and second ends opposed to and spaced from each other in said longitudinal direction,
an outer surface of said first end overlaps an inner surface of said front belt member in said front waist region to define a first overlapping region, and an outer surface of said second end overlaps an inner surface of said rear belt member in said rear waist region to define a second overlapping region, said waist contractile members extend partially across at least one of said first overlapping region and said second overlapping region, said liquid-absorbent structure is joined to said front and rear belt members at least in said first overlapping region or said second overlapping regions by means of joint zones extending in said height direction and arranged intermittently in said circumferential direction, and a joint-free zone where said liquid-absorbent structure is free of attachment to said front and rear belt members is arranged between each pair of adjacent said joint zones and defines vent channels for allowing said crotch region to be in fluid-communication with said front and rear waist regions.

10. The absorbent article according to claim 9, wherein the joint zones are elongated in the longitudinal direction and transversely arranged with respect to the waist contractile members.

11. The absorbent article according to claim 10, wherein the joint zones comprise first joint zones continuously extending in the longitudinal direction and second joint zones intermittently arranged in the longitudinal direction.

12. The absorbent article according to claim 11, wherein the front and rear belt members comprise through-holes extending through inner and outer sheets defining the corresponding front and rear belt members for allowing the wearer's skin to be visible from outside in use.

13. The absorbent article according to claim 12, wherein a longitudinal dimension of the first overlapping region where the liquid-absorbent structure overlaps the front belt member is larger than that of the second overlapping region where the liquid-absorbent structure overlaps the rear belt member.

* * * * *